United States Patent [19]
Gordon et al.

[11] Patent Number: 5,958,714
[45] Date of Patent: Sep. 28, 1999

[54] TEST KITS FOR DETERMINING AT LEAST TWO SPECIFIC ANALYTES IN FOODS AND OTHER COMPLEX MATRICES

[75] Inventors: Virginia C. Gordon, Huntington Beach; John T. Sorensen, Costa Mesa; Soheila Mirhashemi; Michael Mittelstein, both of Laguna Niguel; John F. Elias, Buena Park, all of Calif.

[73] Assignee: Safety Associates, Inc., Tustin, Calif.

[21] Appl. No.: 08/723,636

[22] Filed: Oct. 2, 1996

[51] Int. Cl.$^6$ ................................................. G01N 33/53
[52] U.S. Cl. ........................... 435/7.92; 436/518; 422/56; 422/58; 422/102; 210/238
[58] Field of Search ............................ 436/516; 435/280, 435/179, 7.92; 422/56, 58, 102; 210/238

[56] References Cited

U.S. PATENT DOCUMENTS

| | | | |
|---|---|---|---|
| 4,253,848 | 3/1981 | Porter | 23/230 |
| 4,264,728 | 4/1981 | Wilkins | 435/5 |
| 4,360,591 | 11/1982 | Yamada et al. | 435/4 |
| 4,367,285 | 1/1983 | Yamaguchi et al. | 435/28 |
| 4,407,943 | 10/1983 | Cole et al. | 435/7 |
| 4,427,415 | 1/1984 | Cleveland | 436/57 |
| 4,526,690 | 7/1985 | Kiovsky et al. | 210/335 |
| 4,591,550 | 5/1986 | Hafeman et al. | 435/4 |

(List continued on next page.)

OTHER PUBLICATIONS

Mulchandani, Ashok et al, Analyt. Biochem., vol. 225, pp. 277–282, 1985.

Nourooz–Zadeh, J et al, Analy. Biochem, vol. 220, pp. 403–409, 1994.

Michiels, C et al, Toxicology, vol. 66, 1991, pp. 225–234.

Hermes–Lima, M et al, Free Radical Bio. Med., vol. 19(3), pp. 271–280, 1995.

Degousee, N. et al, Analy. Biochem., vol. 224, pp. 524–531, 1995.

Cominacini, L. et al, Biochemica et Biophys. Acta, vol. 1165, 1993, pp. 279–287.

Babizhayev, M.A., Biochimica Biophysica Acta, vol. 1315, 1996, pp. 87–99.

Nourooz–Zadeh, J. et al., J. Agric. Food Chem, 1995, vol. 43, pp. 17–21.

Nourooz–Zadeh, J. et al, Diabetes, vol. 44, Sep. 1995, pp. 1051–1058.

Lizada, MCC et al, Lipids, 1981, vol. 16(3) pp. 189–194.

Passi, S et al, Appl. Microbiol., Biotech vol., 1984, vol. 19, pp. 186–190.

Wolff, S.P., Methods in Enzymology, 1994, vol. 233, pp. 182–189.

*Primary Examiner*—James C. Housel
*Assistant Examiner*—Ginny Allen Portner
*Attorney, Agent, or Firm*—Robert D. Buyan

[57] ABSTRACT

Methods and apparatus for qualitatively or quantitatively determining one or more analytes in matrices such as foods, biological fluids, etc. An embodiment for determination of a single analyte comprises a sample receiving vessel, a first membrane and a reagent-containing well. The prepared sample passes through the first membrane whereby extraneous matter is removed, and a filtrate enters the reagent-containing well to provide a filtrate-reagent admixture from which the analyte may be determined. An embodiment for determination for multiple analytes includes one or more additional membranes in series with the first membrane, each such additional membrane being operative to capture one or more analytes. Each of the additional analytes may then be eluted from the membrane upon which it has been captured, into a separate reagent-containing well to provide eluant-reagent admixture from which each desired analyte may be determined. Formulations for preparation additives are also included. Additionally, there's provided an embodiment of above-described invention for determination of an analyte which is present in a matrix at low (e.g., sub-detectable) levels, wherein the filter of the apparatus is utilized to capture and concentrate the analyte, to provide a filtrate-reagent admixture wherein the analyte is present at detectable concentration.

14 Claims, 11 Drawing Sheets

U.S. PATENT DOCUMENTS

| | | | |
|---|---|---|---|
| 4,591,556 | 5/1986 | Saxholm | 435/33 |
| 4,642,220 | 2/1987 | Bjorkman | 422/101 |
| 4,657,856 | 4/1987 | Terada et al. | 435/28 |
| 4,734,192 | 3/1988 | Champion | 210/335 |
| 4,753,775 | 6/1988 | Ebersole et al. | 422/81 |
| 4,797,259 | 1/1989 | Matkovich et al. | 422/101 |
| 4,849,330 | 7/1989 | Humphries et al. | 435/4 |
| 4,851,353 | 7/1989 | Miike et al. | 436/71 |
| 4,874,691 | 10/1989 | Chandler | 435/7 |
| 4,900,680 | 2/1990 | Miyazawa et al. | 436/71 |
| 4,902,481 | 2/1990 | Clark et al. | 422/101 |
| 4,914,020 | 4/1990 | Ared et al. | 435/4 |
| 5,035,861 | 7/1991 | Grandone | 422/64 |
| 5,057,438 | 10/1991 | Imai et al. | 436/516 |
| 5,061,633 | 10/1991 | Meguro et al. | 436/71 |
| 5,064,541 | 11/1991 | Jeng et al. | 210/767 |
| 5,077,217 | 12/1991 | Matson et al. | 435/280 |
| 5,108,704 | 4/1992 | Bowers | 422/70 |
| 5,185,246 | 2/1993 | Deutsch | 435/7.21 |
| 5,202,268 | 4/1993 | Kuhn et al. | 436/828 |
| 5,208,161 | 5/1993 | Saunders et al. | 435/286 |
| 5,239,258 | 8/1993 | Kauffman | 324/71.1 |
| 5,264,346 | 11/1993 | Chen | 435/25 |
| 5,283,039 | 2/1994 | Aysta | 422/104 |
| 5,288,636 | 2/1994 | Pollmann et al. | 436/288 |
| 5,328,847 | 7/1994 | Case et al. | 435/291 |
| 5,529,752 | 6/1996 | Pontis et al. | 422/63 |
| 5,620,897 | 4/1997 | Zappe | 436/23 |
| 5,670,374 | 9/1997 | Thornton et al. | 436/23 |

| ANALYTES | | TYPICAL MATRIX | MEMBRANES | | | REAGENTS | | | DETECTION METHOD |
|---|---|---|---|---|---|---|---|---|---|
| | | | $M_1$ | $M_2$ | $M_3$ | $R_1$ | $R_2$ | $R_3$ | |
| 1) Lipid Peroxides | (LPO) | Fatty Foods/Oils | Microporous Mixed Cellulose Ester Film (0.45μ) | Polyamide (0.2μ) (Captures Aldehydes) | None | Xylenol Orange (For LPO) | Methyl Indole (For LA) | None | UV-Visible Spectrophotometry for both LPO and LA |
| 2) Lipid Aldehydes | (LA) | | | | | | | | |
| 1) Lipid Peroxides | (LPO) | Peanuts, Peanut Paste | Microporous PVDF (0.45μ) | Silica Glass (0.2-0.45μ) (Captures LPO) | None | Methyl Indole with Methane Sulfonic Acid (For HEX) | Xylenol Orange (For LPO) | None | UV-Visible Spectrophotometry for both HEX and LPO |
| 2) Hexanal | (HEX) | | | | | | | | |
| 1) Lipid Peroxides | (LPO) | Fish | Microporous Mixed Cellulose Ester Film (0.45μ) | DEAE Cellulose (Captures MA) | Silica Glass (0.2-0.45μ) (Captures LPO) | Histiminase/ Peroxidase Mixture (For HIS) | Methyl Indole (For MA) | Xylenol Orange (For LPO) | UV-Visible Spectrophotometry for HIS, MA and LPO |
| 2) Malonaldehyde | (MA) | | | | | | | | |
| 3) Histamine | (HIS) | | | | | | | | |
| 1) Lipid Peroxides | (LPO) | Dairy Products | Microporous Nylon (0.45μ) | Nitrocellulose coated with antibody to CLA (Captures CLA) | None | Xylenol Orange (For LPO) | Fat Red Dye (For CLA) | None | UV-Visible Spectrophotometry for LPO Enzyme Immunoassay for CLA |
| 2) Conjugated Linoleic Acid | (CLA) | | | | | | | | |
| 1) Lipid Peroxides | (LPO) | Foods Rich in Cholesterol | Microporous Nylon (0.45μ) | Nitrocellulose coated with antibody to CO (Captures CO) | None | Xylenol Orange (For LPO) | 10% N,N-Dimethyl Phenylene Diamine (For CO) | None | UV-Visible Spectrophotometry for LPO Enzyme Immunoassay for CO |
| 2) Cholesterol Oxides | (CO) | | | | | | | | |
| 1) Sulfites | (SULF) | Beer, Wine | Microporous Mixed Cellulose Ester Film (0.45μ) | DEAE Cellulose (Captures SULF and SULF-ALD) | None | Methyl Indole (For C=O) | Sulfite Oxidase (At Alkaline pH for SULF-C=O) (At Acid pH for free SULF) | None | UV-Visible Spectrophotometry for SULF, C=O and SULF-C=O |
| 2) Free Aldehydes | (C=O) | | | | | | | | |
| 3) Sulfite-bound Aldehydes | (SULF-C=O) | | | | | | | | |

| ANALYTES | TYPICAL MATRIX | MEMBRANES | | | REAGENTS | | | DETECTION METHOD |
|---|---|---|---|---|---|---|---|---|
| | | $M_1$ | $M_2$ | $M_3$ | $R_1$ | $R_2$ | $R_3$ | |
| 1) Sulfites (SULF)<br>2) Bromates (BRM) | Beer, Wine, Bread | Microporous Polycarbonate Film | Polyamide Film (Captures Organohalides) | None | Sulfite Oxidase (For SULF) | Starch Solution (For BRM) | None | UV-Visible Spectrophotometry for SULF<br>Titrate with Iodine to determine BRM ("Bromine Clock") |
| Clenbuterol (CB) | Meats | Microporous nitrocellulose or mixed cellulose ester film which is free of non-ionic (Triton) surfactant | Nitrocellulose coated with Antibody to CB (Captures & Concentrates CB) | None | None | Enzyme which Conjugates CB (For CB) | None | Enzyme Immunoassay for CB |
| 1) Alachlor Herbacide (AL)<br>2) All Chloroacetamide Herbacides (CLASS) | Fruits, Vegetables | Low Extractable HATF | Nitrocellulose or Polypropylene coated with antibody to AL (Captures AL) | None | Ethylchloroformate (For CLASS) | Ethylchloroformate (For AL) | None | UV-Visible Spectrophotometry for AL and CLASS |
| 1) Fusarium $T_2$ Mycotoxin ($FT_2$)<br>2) Zearalenone Mycotoxin (ZE) | Grains | Microporous PVDF (0.45μ) | PVDF with Antibody to $FT_2$ bound by Glutaraldehyde (Captures $FT_2$) | PVDF coated with Antibody for ZE (Captures ZE) | Horseradish Peroxidase + Antibody Conjugate (For $FT_2$) | Horseradish Peroxidase + Antibody Conjugate | None | Enzyme Immunoassays for $FT_2$ and ZE |
| 1) Malonaldehyde (MDA)<br>2) Lipid Peroxides (LPO)<br>3) Xanthine (Xa) | Fish, Beans, Coffee | Microporous PVDF (0.2 or 0.45μ) | Polypropylene Matrix with Hydrophobic Affinity or Silica Fused Glass Fiber (Captures LPO) | PVDF coated with Xanthine Oxydase (Captures Xa) | Methyl Indole (For MDA) | Xanthine Oxydase (For LPO) | Peroxidase (For Xa) | UV-Visible Spectrophotometry for MA, LPO and Xa |

| SCHLEICHER & SCHUELL, GmbH<br>P.O. Box 4, D37582, Dassel, Germany | APPLICATION<br>Removal of solid matter, proteins > .45 mm |
|---|---|
| 1. Cellulose Acetate, 0.45 um's 25 mm discs - 23710 | Removal of solid matter, proteins |
| 2. Polyvinylidene Fluoride, 0.2 um's, 25 mm disks - 413006 | Antibody coating |
| 3. NA45 DEAE Cellulose Membrane, 0.45 um's, 25 mm discs - 23310 | Capture aldehydes |
| 4. NA45 DEAE Cellulose Membrane, 0.45 um's, 4x5¼ inches-23430 | Capture of malonaldehyde, sulfites, sulfite-bound aldehydes |
| 5. Nylon, 0.45 um's, 25 mm discs - 00130 | Removal of solid matter, proteins > .45 mm |
| 6. Nylon, 0.2 um's, 25 mm discs - 00030 | Removal of solid matter, proteins > .2 mm |
| 7. NL Polyamide | Capture organohalides |
| 8. PC Polycarbonate | Capture aldehydes |
| PORETICS CORPORATION<br>111 A Lindbergh Ave., Livermore, CA 94550 | APPLICATION |
| 1. MicroPrep, PTFE, PP, NS, 0.2 um's, 13 mm - 97844 | Capture compounds having fatty acid chains lipid peroxides |
| 2. MicroSpin, Nylon, 0.45 um's, Micro-Cent. Tubes-97795 | Removal of solid matter, proteins |
| 3. Ultra-Spin, CTA, PP, S, 10k MWCO, Micro-Cent Tubes -97771 | Removal of solid matter, proteins |
| 4. Silver Membranes, 0.45 um's, 25 mm - 51133 | Capture of volatiles |
| 5. Polycarbonate Membranes, 0.4 um's, 25 mm PVP Free - 11030 | Capture aldehydes |
| 6. Polycarbonate Membranes, 0.4 um's, 25 mm, AOX - 11027 | Capture chlorinated molecules |
| 7. Polycarbonate Membranes, 0.45 um's, 47 mm, Low extr. - 13035 | Capture aldehydes |
| 8. Polycarbonate Membranes, 0.2 um's, 8" x 10", PVP Free - 19416 | Capture aldehydes |
| MILLIPORE CORPORATION<br>80 Ashby Rd., Bedford, Ma 01730-2271 | APPLICATION |
| 1. Isopore, 0.1 um's, 25 mm discs - VCTP 025 00 | Removal of solid matter proteins |
| 2. Immobilon-CD, 0.45 um's, 25 mm discs, Cationically charged (hydrophilic PVDF) - ICDM 025 00 | Removal of solid matter proteins |
| 3. Low Water Extractable (TF) filters, 0.45 um's, 25 mm discs - HATF 025 00 | Removal of solid matter without binding organic molecules |
| 4. Hydrophilic Durapore, 0.45 um's, 25 mm discs -HVL-025 00 | Removal of solid matter proteins |
| 5. Immobilon (hydrophobic PVDF) high protein binding, 0.45 um's, 25 mm discs - ISEQ 025 00 | Removal of proteins |
| 6. Isopore, HTTP (polycarbonate), 0.4 um's, 25 mm discs - HTTP 025 00 | Capture aldehydes |
| 7. Immobilon-P Transfer Membranes (PVDF), 0.45 um's, 15 cm x 15 cm - IPVH 151 50 | Coating with antibodies to capture or remove antibody-specific compounds |
| 8. Immobilon Transfer Membranes (PVDF), 0.45 um's, 15 cm x 15 cm - ICDM 151 50 | Coating with anitbodies to caputre or remove antibody-specific compounds |
| 9. Immobilon NC Pure, 0.22 um's, 15 cm x 15 cm - INCP 151 50 | Coating with antibodies to capture or remove antibody-specific compounds |
| 10. Immobilon-NC(Surfactant free), 0.45, um's, 15cm x 15cm HATF 151 50 | Coating with antibodies to capture or remove antibody-specific compounds |
| 11. MultiScreen - DEAE Anion Exchange Paper Opaque 96 well plates - MADE NOB 10 | Capture aldehydes |
| 12. MultiScreen - Phospho Cellulose Cation Exchange Paper, Opaque 96 well plates, MAPH NOB 10 | Bind lipid peroxides for capture |
| WHATMAN, INC.<br>6 Just Road, Fairfield, NJ 07004 | APPLICATION |
| 1. GF/A - Glass Microfibre Filters, 25 mm - 1820 025 | Capture of lipid peroxides small amount |
| 2. GF/B - Glass Microfibre Filters, 25 mm - 1821 025 | Capture of lipid peroxides medium amount |
| 3. GF/D - Glass Microfibre Filters, 25 mm - 1823 025 | Capture of lipid peroxides large amount |

Fig. 6

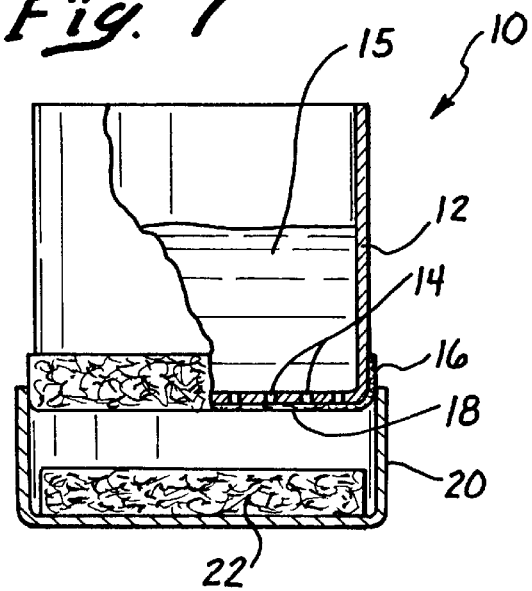
Fig. 7
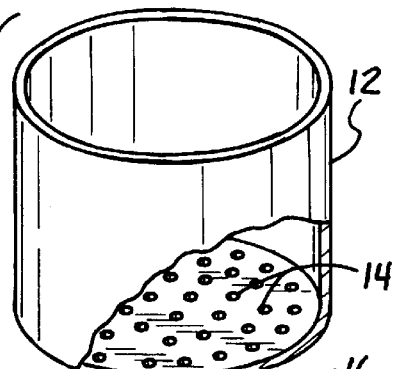
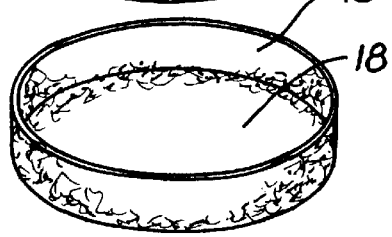
Fig. 7a
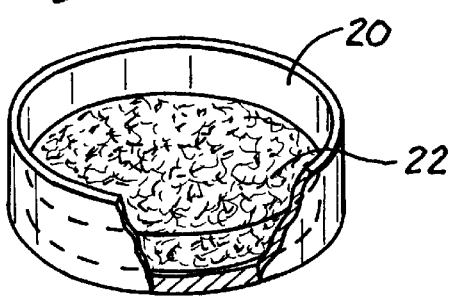
Fig. 7b
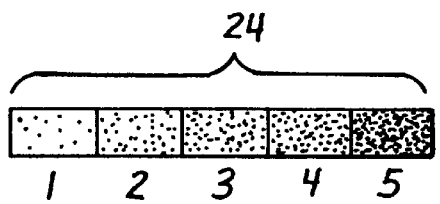
Fig. 7c

TEST KITS FOR DETERMINING AT LEAST TWO SPECIFIC ANALYTES IN FOODS AND OTHER COMPLEX MATRICES

FIELD OF THE INVENTION

The present invention pertains generally to methods and apparatus for analytical chemistry, and more particularly to test kits and methods for qualitatively or quantitatively determining one or more analytes present within a matrix such as a food substance or biological fluid.

BACKGROUND OF THE INVENTION

It is routinely desirable to test for the presence of specific analytes in substances which are intended for human consumption or application to the human body (e.g., foods, beverages, cosmetics, toiletries, topical solutions, contact lens solutions, pharmaceutical preparations, etc.) to confirm that such substances are fresh (i.e., not degraded), pure and free of contamination. Additionally, it is often desirable to test for the presence of specific analytes in samples of biological fluids (e.g., blood, plasma, serum, urine, saliva, bile, lymph, etc.) which have been extracted from the human body.

However, the analytical techniques which have heretofore been utilized to quantitatively or qualitatively test for specific analytes in complex matrices are often problematic, due to the fact that such substances may contain many diverse physical and/or chemical species, some or all of which may interfere with the intended analysis. Thus, it is frequently necessary for the test substance to be subjected to extensive sample preparation steps, in order to isolate and/or concentrate the particular analyte(s) of interest, prior to actually proceeding with analytical determination of the desired analyte(s). Moreover, in instances where the test substance is a solid material (e.g., food) it is often necessary to chop or grind the solid material into particles, and to extract the desired analyte(s) from such particles by adding one or more liquid digestants, solvents or other fluids to form a slurry or suspension, and thereafter performing a "clean up" of the slurry or suspension by filtration or centrifugation to separate the analyte containing liquid from the extraneous solid matter.

In instances where multiple analytes are to be determined, it is often necessary to perform several separate, time consuming, analytical procedures (e.g., gas chromatography (GC), high performance liquid chromatography (HPLC) or other analytical chemistry procedures) on aliquots or extracts of the test substance, in order to generate the desired multiple analyte data.

Thus, the traditional methods for determining the presence of, or detecting specific analyte(s) in complex matrices (e.g., substances which contain matter other than the desired analyze(s)) can be quite time consuming, skill intensive and expensive.

A. Testing of Foods to Ensure Purity and Wholesomeness

It is frequently desirable to detect or quantify, in foods, one or more particular analyte(s) which are indicative of the freshness or quality of the food. In routine quality control testing of foods, it is common practice to test for the presence of various contaminates, additives, degradation products, and/or chemical markers of microbial infestation (e.g., bacterial endotoxins, mycotoxins, etc.). However, the current methods by which such quality control testing of food is accomplished are typically either: a) complex and skill-intensive analytical chemistry procedures or b) highly subjective and qualitative sensory evaluations (e.g., smell test, taste test, appearance, etc.).

B. Oxidative Degradation of Fatty Foods

As fatty acids within foods oxidize, relatively unstable lipid hydroperoxides are formed. The presence of these lipid hydroperoxides typically do not affect the smell or flavor of the food in any discernible way. These lipid hydroperoxides then further decompose to form relatively stable lipid aldehydes (e.g., malonaldehyde). The accumulation of lipid aldehydes within the food can give rise to off-odors and off-flavor of the food. Thus, it is difficult or impossible to detect the presence of abnormally high lipid hydroperoxide levels in foods by smell or taste testing, despite the fact that such elevated lipid hydroperoxide levels may indicate that the fats of the food have begun to undergo oxidative degradation and are becoming rancid. Moreover, inadvertent consumption of these undetected lipid hydroperoxides may adversely affect the health of human beings due to the fact that such hydroperoxides are believed to play a significant role in the pathogenesis of atheroschlortic vascular disease and/or other health problems.

Various analytical techniques have previously been available to detect the presence of the lipid hydroperoxides and/or lipid aldehydes in foods, many of which involve the separate steps of a) extraction, b) clean-up, c) derivitization, d) analysis and e) detection. These previously utilized analytical techniques for detecting lipid hydroperoxides and lipid aldehydes in foods are typically expensive, time consuming, and require considerable expertise and training.

In particular, one frequently used analytical procedure for lipid aldehydes, known as the thiobarbituric acid (TBA) assay, requires that the lipid aldehydes be extracted and isolated in an analytical solution and subsequently reacted with thiobarbituric acid to give a red fluorescent adduct, which exhibits maximum UV absorbance at 532 nm. The initial extraction and isolation of the lipid aldehydes frequently requires laborious sample preparation steps. Moreover, the TBA assay is not specific for malonaldehyde (the primary lipid aldehyde in rancid fats), but rather may react with other aldehydes or other chemical species which are not indicative of rancidity. Thus, the reliability and meaningfullness of the TBA assay for assessing rancidity in foods is controversial.

Other, more complicated analytical methods have been utilized to detect lipid hydroperoxides and/or rancidity-indicating aldehydes in foods, including procedures based on electron spin resonance, high-performance liquid chromatography, and liquid chromatography-chemiluminescence techniques. However, these other analytical methodologies for assessing rancidity of fats can be extremely expensive, time consuming, and labor-intensive.

Examples of previously-known analytical techniques or other evaluations for determining lipid aldehydes in foods or other complex matrices include those described in the following publications: Nollet, L. M L.(ed.), *Handbook of Food Analysis,* Marcel Decker, Inc. (1996); Warner, K., *Sensory Evaluations Based on Odor and Flavor; Methods to Assess Quality and Stability of Oils and Fat Containing Foods,* Pgs. 49–75, AOCS Champaign, Ill. (1995); Evans, C. D., *Analysis of Headspace Volatiles by Gas Chromatography,* Proceedings of AOCS October Meeting (Pg. 15–18) (1967); Dugan, L., *Kreis Test for C=O Groups With Phloroglucinol,* Journal of the American Oil Chemists Society 32, Pg. 605 (1955).

Examples of previously-known methods for determining lipid peroxides in foods or other complex matrices include those described in the following publications: Nollet, L. M. L.(ed), *Handbook of Food Analysis,* Marcel Decker, Inc. (1996); *Methods to Determine Lipid Peroxides by Titration*

*Method,* Journal of the American Oil Chemists Society, Vol. 26, Pg., 345 (1949); Gray, J. I., *Conjugated Diene Measurements at 230–375 nm,* Journal of the American Oil Chemists Society, Vol. 45, Pg. 632 (1978), Halliwell B, Gutteridge J M C. *Free radicals in biology and medicine,* 2nd ed. Oxford,d UK: University Press, 1989:543pp; Gutteridge J M C, Halliwell B. *The measurement and mechanisms of lipid peroxidation in biological systems,* Trends Biochem Sci 1990;15:129–35; Gutteridge J M C. *Lipid peroxidation: some problems and concepts,* in ed. (*Oxygen radicals and tissue injury*). Halliwell B., Bethesda, Md.:FASEB, 1977:9–19; Gutteridge J M C, Kerry P J. *Detection by fluorescence of peroxides and carbonyls in samples of aracyidonic acid.* Br J Pharmacol 1982;76:459–61; Gutteridge J M C. *Iron promoters of the Fenton reaction and lipid peroxidation can be released from haemoglobin by peroxides.* FEBS Lett 1986;20:291–5.; Gutteridge J M C, Beard A P C, Quinlan G J. *Superoxide-dependant lipid peroxidation: problems with the use of catalase as a specific probe for Fenton-driven hydroxyl radicals.* Biochem Biophys Res Commun 1983;117:901–7.; Halliwell B, Gutteridge J M C. *Lipid peroxidation, oxygen radicals, cell damage and antioxidant therapy.* Lancet 1974;1:1396–8; Halliwell B, Gutteridge J M C> *The definition and measurement of antioxidants in biological systems.* Free Radic Bio Med 1995;18:125–6; Gutteridge J M C. *The antioxidant activity of haptoglobin towards haemoglobin stimulated lipid peroxidation.* Biochim Biophys Acta. U.S. Pat. No. 5,320,725, entitled "Electrode and method for the detection of hydrogen peroxide," (Gregg et al.), Assignee: E. Heller & Company, Austin, Tex.; U.S. Pat. No. 4,851,353, entitled "Method and test composition for determination of lipid peroxide," (A. Miike, et al.), Assignee Kyowa Hakko Kogyo Co., Ltd., Tokyo, Japan; U.S. Pat. No. 4,900,680, entitled "Method and apparatus for measuring lipid peroxide," (T. Miyazawa, et al.), Assignee: Tobuku Electronic Industrial Co., Ltd., Sendai, Japan; U.S. Pat. No. 5,061,633, entitled "Method for analyzing lipid peroxides using aromatic phosphines", (H. Meguro, et al.) , Assignee: Tosoh Corporation, Japan; U.S. Pat. No. 4,367,285, entitled "Assaying lipid peroxide in lipid composition," U.S. Pat. No. 4,367,285, entitled "Assaying lipid peroxide in lipid composition," (T. Yamaguchi, et al.), Assignee: Toyo Jozo Company, Ltd., Tokyo, Japan; U.S. Pat. No. 4,657,856, entitled "Glutathione peroxidase, process for production thereof, method and composition for the quantitative determination of lipid peroxide," (O. Terada, et al.), Assignee: Kyowa Hakko Xogyo Co., Ltd., Tokyo, Japan.

The analysis of lipid peroxides and/or lipid aldehydes in foods or other matrices is not limited to applications wherein it is desired to determine whether the food or other matrix has undergone oxidative degradation. In fact, it is often desirable to test for lipid peroxides and/or lipid aldehydes as a means of determining the resistance to oxidation or "antioxidant status" of a particular food product or other formulation. Such testing for antioxidant status provides a means for determining whether a food or other type of product is likely to undergo oxidative degradation under the production, shipping, storage and use conditions to which the food or other product will be exposed. In order to mimic extreme oxidative conditions, such testing for antioxidant status is often performed in conjunction with an oxidative challenge, such as the purposeful addition of an oxidation promoting chemical to the test formulation, or by exposing the test material to high-intensity light or heat.

In this regard, antioxidants are often added to food products, cosmetics or other formulations to prevent oxidative degradation or deterioration during production, storage and/or cooking. It is critical, however, that such antioxidant additives be present at sufficient concentrations to prevent potentially toxic lipid peroxides and/or aldehydes from forming under the intended production, storage and/or cooking conditions. Thus, in the development of food and/or other product formulations it is often necessary to test various types, combinations and/or concentrations of antioxidant additives in order to determine which formulation(s) are best suited for the intended production, storage and/or cooking conditions. Moreover, it is often desirable to perform analyses of lipid peroxide and/or lipid aldehyde concentrations in previously-prepared food and/or product formulations as a means of identifying and testing new synthetic and/or natural antioxidants which may be usable to prevent oxidative degradation of such products.

To fully understand the propensity for and state of oxidative degradation of a material (e.g., a food), it is desirable to assay the material for lipid peroxide concentration, lipid aldehyde concentration, and resistance to oxidation, at least two (2) temperatures, at 2 or more time points over 0 to 48 hours. The evaluation temperatures may typically include 56° C. and 37° C., since these temperatures approximate the extremes of usual shelf life conditions. Higher temperatures cause changes in the dynamics of lipid peroxide and lipid aldehyde formation. The time to reach the end points of sudden increases in lipid peroxide and/or lipid aldehyde concentrations is predicative of resistance to oxidation. Also, lipid peroxides are more stable in some matrices than others, so the profile of their values over time, and the relative increase or decrease of their breakdown products, provides complete information about the status of oxidative degradation of the matrix.

When used in foods, the quantity of some antioxidant additives may be subject to governmental regulation, especially in formulations wherein synthetic antioxidant additives are being utilized. Thus, in such situations, it is typically desirable to perform lipid peroxide and/or lipid aldehyde analyses as means of determining the minimum amount(s) of particular antioxidant additives which must be added to a particular formulation to provide the desired antioxidant affect and/or to identify non-regulated natural alternatives to governmental regulated synthetic additive. Thus, the detection and/or analysis of lipid peroxides and lipid aldehydes in foods and other formulations is often carried out for various product/formulation development or research purposes, as well as for quality control testing of the freshness and wholesomeness of the food or other product.

Because the previously-known analytical methods for determining lipid aldehyde and/or lipid peroxide concentrations in foods have involved relatively complex chemical analytical procedures which may be too complex or too skill-intensive for untrained personnel, there exists a need in the art for the development of simple test kits capable of rapidly and reproducible determining the presence and/or concentrations of lipid peroxides and lipid aldehydes in foods and other complex matrices, so that relatively untrained personnel may perform such determinations in a reliable, cost effective manner.

C. Chemical Contaminants in Foods

Many types of chemical contaminants, such as pesticides, herbicides, excessive concentrations of food additives, etc., may be present in foods. It is highly desirable to detect the presence of such chemical contaminants prior to sale or consumption of the affected foods. Unfortunately, the analytical methodologies which have heretofore been utilized for determining the presence of such chemical contaminants in foods have typically required laborious, skill-intensive analytical chemical procedures which are too complex or too skill-intensive to be performed by untrained personnel.

Examples of the types of analytical chemical procedures which have heretofore been utilized to quantitatively or qualitatively determine the presence of chemical contaminants (e.g., herbicides, pesticides, additives) in food include those described in the following publications: Monier, W. G., *Williams Determination of Sulfite,* Analyst, Vol. 52, Pg. 415, (1927); Rothenfusser, S., Lebensm Untero Forsch, Vol. 58, Pg. 98 (1929); Nollet, L. M. L.(ed.), *Handbook of Food Analysis,* Marcel Decker, Inc., Pg. 507, (1996); Tekel, J. et al., *HPLC Analysis of Herbicides,* Journal of Chromatography, Vol. 643, Pg. 291, (1993).

D. Drug Residues in Meats and Animal Products

Modern veterinary practice utilizes various drugs and pharmaceutical agents which, when administered to cattle, dairy cows, chickens and other farm animals, will maximize and improve the rate of growth and/or productivity of such animals. For example, antibiotics, corticosteroids and certain beta-adrenergic agonists are sometimes administered to meat-producing animals (e.g., cattle, hogs, chickens, lambs) to accelerate weight gain. Similarly, antibiotics are sometimes administered to farm animals as prophylaxis against or treatment for infectious disease (e.g., mastitis in dairy cows). It is typically necessary to cease administration of these pharmaceutical agents a specified time period prior to slaughtering of the animal or obtainment of food products (milk, eggs) therefrom, to ensure that the meat or other animal products will not contain excessive or potentially toxic levels of these pharmaceutical agents. Thus, it is desirable to routinely test the meats and other food products obtained from drug-treated animals to confirm that such meats and/or food products are not contaminated with excessive levels of these pharmaceutical agents.

The analytical procedures which have heretofore been utilized to determine the concentrations of drugs such as antibiotics, corticosteroids, and/or beta-adrenergic agonists in meats or animal products (e.g., milk, eggs) have been relatively complex, time-consuming and skill-intensive procedures. Examples of previously known analytical procedures for determining the concentrations of antibiotics, corticosteroids, and/or beta-adrenergic agonists in meats or other animal products include those described in the following publications: Cole, R. J.(ed.), *Modern Methods in Analysis and Structural Elucidation,* Pg. 239, 265, 293, Academic Press (1986); Boison, J. O., Analysis Myrotoxins, Journal of Chromatography, Vol. 629, Pg. 171, (1992); Adams, A. et al., Proc. 2nd International Symposium on Hormone and Veterinary Drug Residue Analysis, Pg. 50, (1994); and, Tomlin, Conn.(ed), British Crop Protection Council; Farniham, Surrey, U.K. (1994).

E. Chemical Markers of Microbial Contamination

Some microbes, including certain viruses, bacteria and fungi are known to secrete toxins, enzymes or other chemical markers which may be directly toxic to humans if consumed and/or are clearly indicative of the presence of such microbial contamination in a particular foods. Examples of such chemical markers of microbial contamination include clostridium botulinum toxins, toxins secreted by fusarium $T_2$ and zearalenone fungi which affect corn and other grains, and endotoxins or metabolites given off by certain pathogenic bacteria (e.g., salmonella, lysteria, *E. coli,* etc.).

Standard microbiological culture techniques can sometimes be utilized to identify the presence of microbial contaminants in foods, but such microbiological culture techniques typically must be performed by highly trained individuals, and often require a relatively long incubation time.

Similarly, analytical chemical methods can be used for determining or quantifying the presence of the chemical markers (e.g., endotoxins, toxins, metabolites, etc.) of certain pathogenic microbes, but such chemical analytical procedures are also relatively complex, time consuming, and require a substantial amount of technical skill and training.

In view of the foregoing problems, limitations and needs associated with detection and/or quantification of specific analytes (e.g., detection of degradation products, antioxidant status, drug residues, chemical contaminants or markers of microbial contamination, in foods or other matrices) in complex matrices there exists a need in the art for the development of simplified, cost-effective, reliable and reproducible methods and apparatus for performing such detectings and/or quantifications in complex matrices (e.g., foods, biological fluids, etc.).

SUMMARY OF THE INVENTION

The present invention provides test kits for qualitatively or quantitatively determining one or more analytes in matrices such as foods, other solid materials or some biological fluids.

In accordance with one embodiment of the invention, there is provided a simple test kit for determining the presence of a single analyte, such test kit comprising; a) a sample receiving vessel, b) a membrane and c) a reagent-containing well. The test sample is initially prepared (e.g., chopped or ground if a solid) and is deposited in the sample-receiving vessel along with any desired diluent, digestion solution (e.g., enzymes), chelators, or chemical modifiers (e.g., antioxidants). The prepared sample is then permitted to drain from the sample-receiving vessel, through the membrane. The type of membrane utilized in each embodiment will be selected based on the type and quantity of matter which is desired to be excluded from the prepared sample matter prior to analysis. In many applications, this initial membrane will be formed of microporous film having pores which are sized to present large particles of solid matter, proteins and other unwanted matter from passing therethrough, but which will allow a filtrate containing the desired analyte to drain into the reagent-containing well. When drained into reagent-containing well, the analyte contained within the filtrate will react with the reagent in a manner which will permit the presence or quantity of analyte to be determined. In many instances, the analyte-reagent reaction will be a color forming reaction such that a visual determination may be made as to whether, or to what degree the desired analyte is present. In other instances, it may be desirable to utilize an analytical instrument to determine the quantity of analyte present in the analyte present in the analyte-reagent solution.

In accordance with other embodiments of the invention, the simple test kit of the above-described character may be adapted for determination of two or more analytes by the addition of one or more additional membranes in series with the first membrane. Each of these additional membranes is operative to capture and hold at least one analyte, while allowing a filtrate containing one or more other analyte(s) to pass therethrough. Each of these additional membranes may subsequently be exposed to a wash or flush solution such that one or more eluants containing each of the additional analytes may be obtained. Each such eluant may subsequently be combined with a reagent to provide an eluant-reagent admixture from which at least one analyte may be determined. In this manner, the present invention is adaptable for the qualitative or quantitative determination of two or more analytes from a single sample.

Further in accordance with the invention, there is provided a method and apparatus for determining one or more analytes which are present in a matrix at low (e.g., sub-detectable) levels. This embodiment of the invention may be in the form of test kit comprising a) a sample receiving vessel, b) an analyte-capturing membrane, and c) a reagent-containing well. A sample containing the analyte is passed through the analyte-capturing membrane such that the desired analyte will be captured by the membrane. Thereafter, a known volume of flush solution is utilized to elute the analyte from the membrane and into the reagent-containing well. In this manner, the analyte will become concentrated in a smaller volume than that of the original matrix, thereby providing an eluant-reagent admixture from which the analyte may be qualitatively or quantitatively determined.

Further objects and advantages of the invention will become apparent to those skilled in the art upon reading and understanding of the following detailed description and consideration of the accompanying drawings.

BRIEF DESCRIPTION OF THE DRAWINGS

FIG. 5 is a table listing different applications, membranes and reagents which may be utilized in accordance with the present invention, to quantitatively or qualitatively detect various different analyte(s) in various different matrices.

FIG. 6 is a table listing examples of commercially available membranes which may be useable for removing or capturing various different substances, in test kits of the present invention.

FIG. 7 is a partial cut-away, elevational view of a basic test apparatus of the present invention usable for detection of single analyte in a prepared matrix, such as food product.

FIG. 7a is an exploded view of the apparatus of FIG. 7.

FIG. 7b is a partial cut-away perspective view of the indicator module portion of the apparatus shown in FIGS. 7 and 7a.

FIG. 7c is a schematic representation of a color indicator chart which may be utilized to visually determine the concentration of the target analyte within the indicator module of FIG. 1b.

DETAILED DESCRIPTION OF THE PREFERRED EMBODIMENTS

The following detailed description, and the accompanying drawings, are provided for purposes of describing and illustrating presently preferred embodiments of the invention only, and are not intended to limit the scope of the invention in any way.

With reference to the drawings, FIGS. 1–5 are directed to the methods of the present invention, while FIGS. 6–9 show presently preferred apparatus which may be used to perform the methods of the present invention.

A. Methods of the Present Invention

The methods of the present invention range in complexity from a basic method whereby the presence of a single analyte may be qualitatively determined to a complex method whereby a plurality of different analytes may be quantitatively determined from a single analytical sample.

i. Method for Determining a Single Analyte

Figure 1:
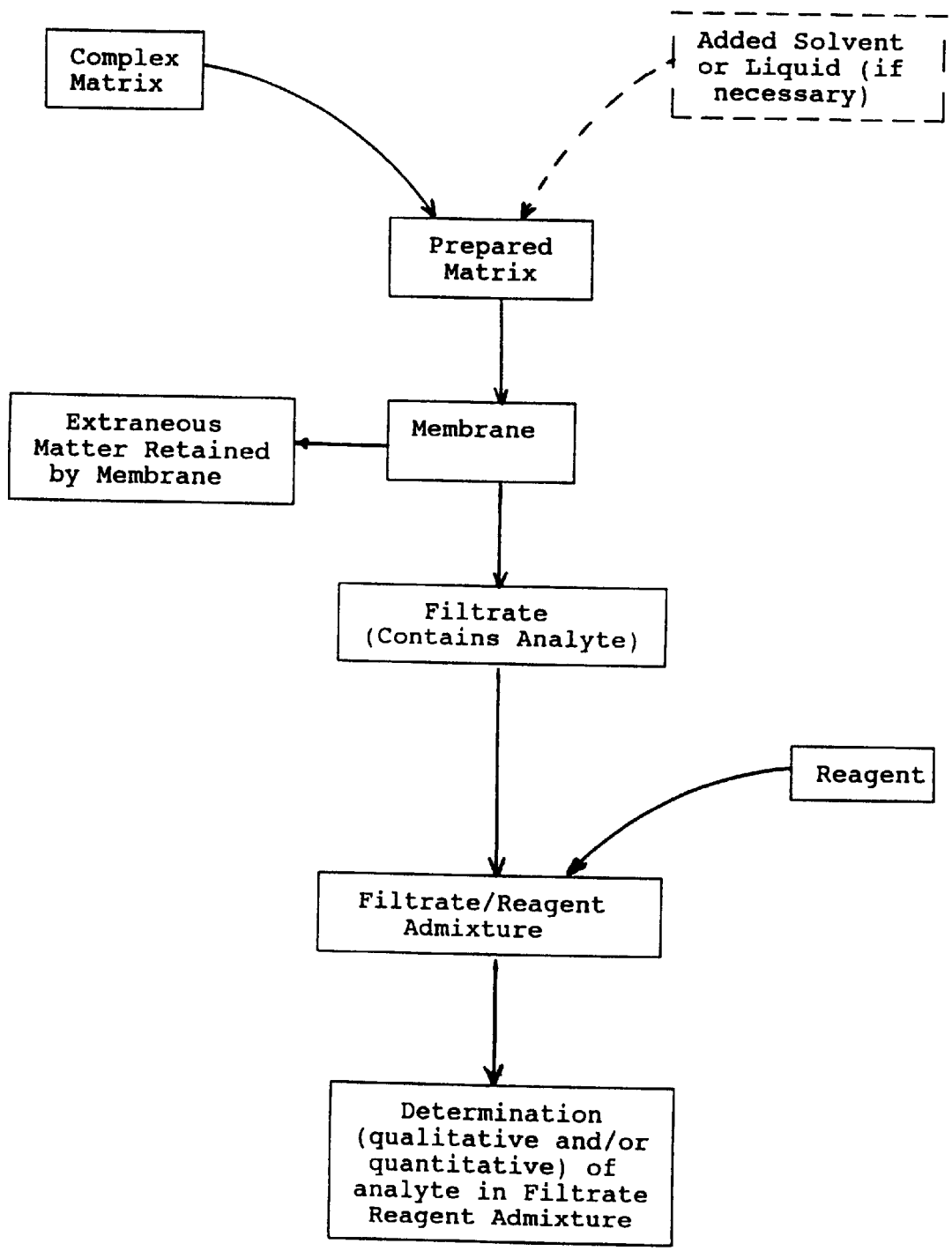
FIG. 1 is a flow diagram of a general method of the present invention, for detecting a single analyte.

FIG. 1 shows a flow diagram of a basic method of the present invention wherein a single analyte may be qualitatively and/or quantitatively determined within a complex matrix (i.e., a matrix which contains one or more materials other than the analyte).

Initially, the complex matrix is prepared and, if necessary, is combined with added solvent or liquid to form a prepared matrix for subsequent processing. In instances where the complex matrix is a solid material (e.g., food) it will typically be necessary to grind or chop the complex matrix and to add a solvent, digestant, or other carrier liquid such that the "prepared matrix" will be in the form of a slurry or suspension.

For many applications of the invention, and in particular those wherein it is desired to detect lipid peroxides and/or lipid aldehydes in food matrices, one or more preparation additives such as digester/stabilizer solution(s) including enzyme(s) and/or stabilizer(s) and/or chelator(s) may be added to the matrix during the preparation step to extract or dissolve the desired analyte(s). Examples of specific digesters which may be included in such solution include lipase enzymes and protease enzymes. Examples of stabilizers which may be included in such solution include BHT, α-tocopherols, propyl gallate and mannitol. Examples of chelators which may be included in such solution include EDTA. One particular digester/stabilizer solution which may be utilized has the following formulation:

Formulation For Digester/Stabilizer Solution

BHT . . . 200 ppm

EDTA . . . 100 ppm

Lipase . . . 5,000 IU/ml

Water . . . QS

In at least some applications of the method, it may be desirable to additionally or alternatively add an emulsifier solution, such as a mixture of alcohols, to increase separation of the analyte(s) from the matrix. In applications wherein the matrix has been subjected to a digestion step, such as by way of the digester/stabilizer solution described hereabove, such emulsifier or diluent solution will typically be added after the digestion has been completed. For analysis of analyte(s) such as fats or oils the diluent solution may comprise formulations such as mixtures of alcohols. One such universal diluent solution which has been discovered to be particularly usable in accordance with the present invention, has the following formulation: and found to be particularly useful in accordance with the present invention:

Formulation For Universal Diluent Solution I

Butanol . . . 2 parts by volume

Isopropanol . . . 1 part by volume

Another such diluent solution, which is particularly useful in applications of the present invention wherein it is desired to determine or quantify lipid derivatives, has the following formulation:

Formulation For Universal Diluent Solution II

USED AFTER DIGESTION

Cyclodextrin . . . 0.5% by weight

Water . . . 99.5% by weight

Thereafter, the prepared matrix is passed through a membrane which removes or retains extraneous matter (e.g., solid particles or interfering substances such as proteins) while allowing a filtrate, which contains the analyte, to pass therethrough. In many instances, the membrane will be in the form of a microporous cellulose or polymer film having a desired pore size (e.g., 20–60 microns) which will filter out large proteins and relatively large solid particles while allowing relatively small solid particles and the accompanying liquid containing the analyte to pass therethrough. One example of a membrane which may be used for this purpose is a membrane formed of mixed cellulose ester film having 0.45 micron pores formed therein (e.g., ME-25 Membrane, Schleicher & Schuell GmbH, P.O. Box 4, D37582, Dassel, Germany).

The analyte-containing filtrate which passes through the membrane is subsequently mixed with one or more reagents to provide a filtrate/reagent admixture from which the desired qualitative and/or quantitative determination of the analyte may be performed.

Thereafter, the filtrate/reagent admixture is subjected to the desired analytical or measurement techniques to provide the intended qualitative and/or quantitative determination of the analyte. In some instances, this determination of the analyte may be made by a simple chemical test whereby a visual indicator (e.g., a color change) will indicate the presence and/or concentration of the analyte. In other instances, the determination of the analyte will be carried out by one or more analytical instruments, such as a colorimeter, spectrophotometer, optical densitometer, etc.

Thus, the general method illustrated in the flow diagram of FIG. 1 provides a means for qualitatively and/or quantitatively measuring an analyte which is present within a complex matrix.

ii. Method For Detecting Multiple Analytes

Figure 2:
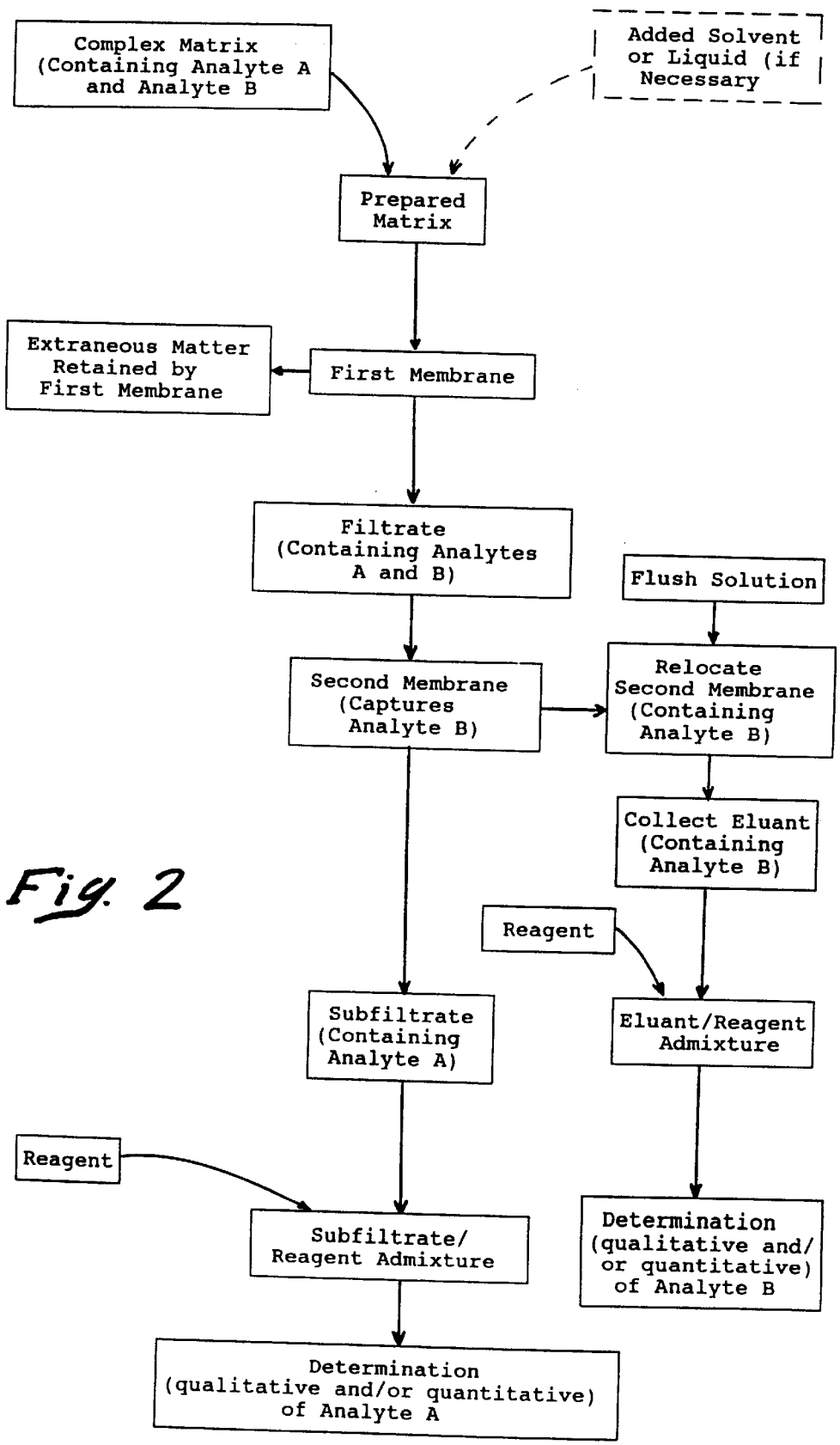
FIG. 2 is a flow diagram of a general method of the present invention, for detecting multiple analytes.

FIG. 2 shows a more elaborate general method of the present invention wherein it is desired to analyze two (2) separate analytes present within a complex matrix. The complex matrix in this example may be the same as that described hereabove with respect to FIG. 1 (e.g., food), and the method of preparing the complex matrix and the optional addition of solvent or liquid may be carried out in the same manner.

Thereafter, the prepared matrix is passed through a first membrane which retains or removes extraneous matter while allowing a filtrate, which contains both analytes a and b, to pass therethrough. As described hereabove, the first membrane may comprise a microporous membrane having known pore size so as to remove particles of solid matter which are larger than the membrane pore size, while allowing smaller particles of solid matter and the accompanying liquid containing Analytes A and B, to pass therethrough. As in the example of FIG. 1, one such membrane may be formed of mixed cellulose ester film (e.g., ME-25 Membrane, Schleicher & Schuell GmbH, P.O. Box 4, D37582, Dassel, Germany).

Thereafter, the filtrate which has passed through the first membrane will be subsequently passed through a second membrane. This second membrane is adapted to capture and hold Analyte B, while allowing a sub-filtrate containing Analyte A to pass therethrough. In this manner, the second membrane serves to separate and remove Analyte B from Analyte A.

The Analyte A-containing sub-filtrate which has passed through the second membrane will be thereafter combined with a reagent to provide a sub-filtrate/reagent admixture from which qualitative and/or quantitative determination of Analyte A may be performed.

Thereafter, the desired qualitative and/or quantitative determination of Analyte A is performed on the sub-filtrate/reagent admixture in the same manner as described hereabove with respect to FIG. 1.

The second membrane, which contains Analyte B, may be removed or relocated and a flush solution, capable of releasing and carrying Analyte B from the second membrane, will be passed therethrough. Such passage of the flush solution through the second membrane will provide an eluant of known volume, which contains Analyte B.

Thereafter, the eluant containing Analyte B is combined with a reagent to provide an eluant/reagent admixture from which Analyte B may be qualitatively and/or quantitatively determined.

Thereafter, the qualitative and/or quantitative determination of Analyte B is performed on the eluant/reagent admixture in the manner described hereabove with respect to FIG. 1.

Thus, the example shown in FIG. 2 provides a method whereby two separate analytes may be qualitatively and/or quantitatively determined in a complex matrix.

It will be appreciated that, although FIG. 2 provides an example wherein only two analytes (e.g., Analyte A and Analyte B) are determined, it will be possible to determine any desired number of analytes in accordance with the present invention by providing additional secondary membranes in series with the "second membrane" shown in FIG. 2, so as to capture and collect each of the desired analytes. Thereafter, flush solutions may be passed through each of these secondary membranes to provide eluants containing each of the individual analytes. Those eluants may then be combined with reagents and subjected to the desired qualitative and/or quantitative determinations for the desired analytes.

iii. Method For Detecting Analyte(s) Which Are Present At Low Concentrations FIG. 3 shows another example of a method of the present invention wherein it is desired to qualitatively or quantitatively determine the presence of a single analyte, which is present in a complex matrix at a concentration below the usual detection limits for the analytical procedure to be used.

Figure 3:
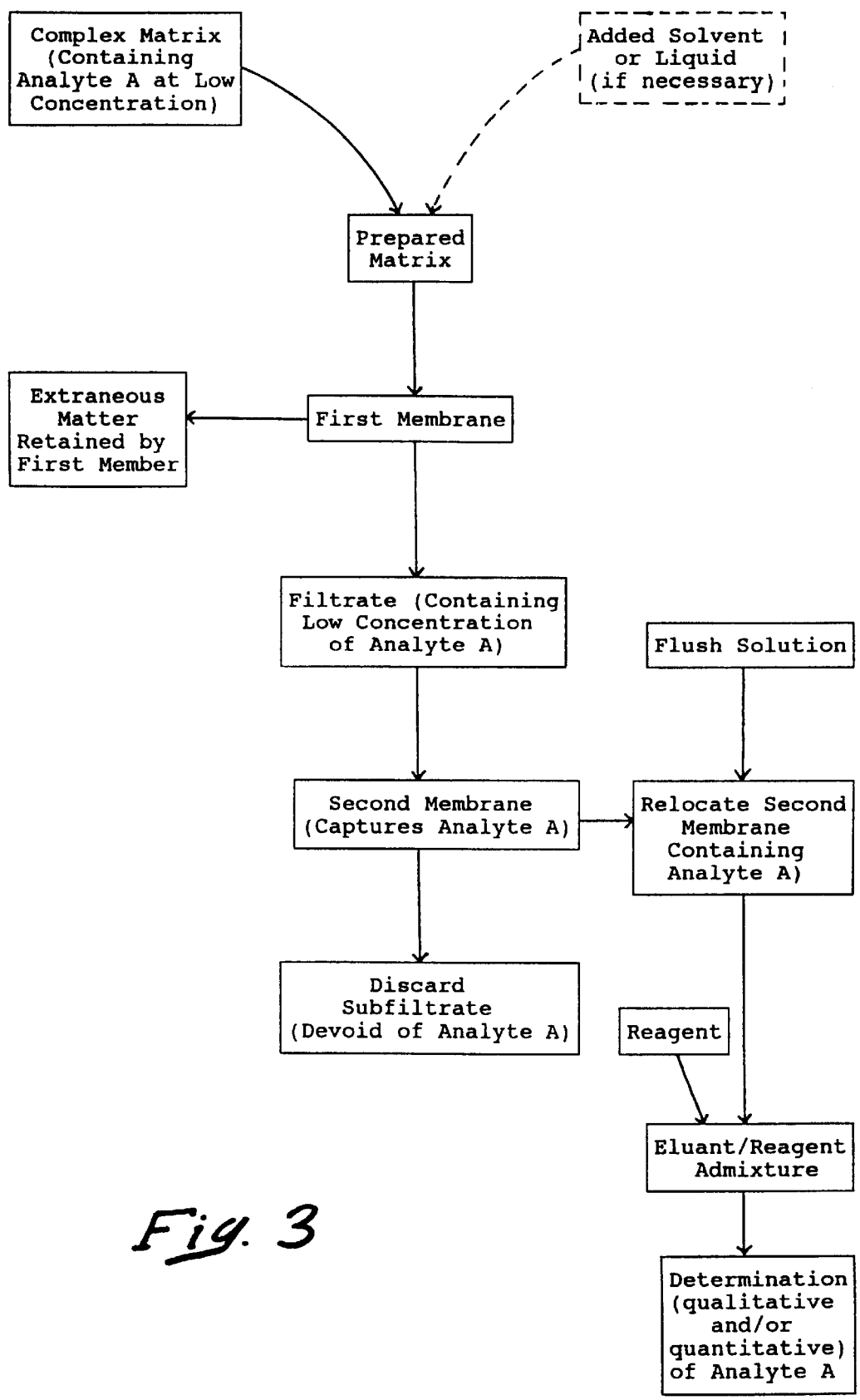
FIG. 3 is a flow diagram of a general method of the present invention, for detecting an analyte which is present at low (e.g., sub-detectable) concentration in a complex matrix.

In this example, shown in FIG. 3, the complex matrix is prepared and optionally combined with solvent or liquid in the same manner as described hereabove with respect to FIGS. 1 and 2.

Thereafter, the prepared matrix is passed through a first membrane which will retain extraneous matter, while allowing a filtrate containing the Analyte A to pass therethrough. This first membrane may be the same type of first membrane described hereabove with respect to FIGS. 1 and 2.

Thereafter, the filtrate, which contains Analyte A, is passed through a second membrane. The second membrane is operative to capture and hold Analyte A, while allowing the remaining fraction(s) of the filtrate to pass therethrough as a sub-filtrate, which is subsequently discarded.

The second membrane, which contains Analyte A, is then relocated and positioned over a well or containment vessel, and a known volume of flush solution is passed therethrough. The volume of flush solution which is passed through the second membrane will be less than the volume of filtrate which had previously been passed through the first membrane. Passage of this flush solution through the second membrane will release and carry Analyte A from the second membrane. In this manner, there is provided an eluant/reagent admixture wherein Analyte A is contained at a concentration which is higher that the original concentration of the Analyte A in the filtrate which passed through the first membrane. Thus, Analyte A is now present in the eluant at a concentration which is high enough to be detected or measured by the desired analytical procedure or method.

Accordingly, the desired qualitative and/or quantitative determination of Analyte A is performed on the eluant/reagent admixture, in the manner described hereabove with respect to FIGS. 1 and 2.

Thereafter, well known mathematical principles may be utilized to calculate the concentration at which Analyte A was present in the original complex matrix, although Analyte A was subsequently concentrated into the eluant/reagent admixture at higher concentrations capable of being detected or determined by the desired analytical procedure.

iv. A Specific Method For Determining Lipid Peroxides In a Food Matrix

Figure 4:
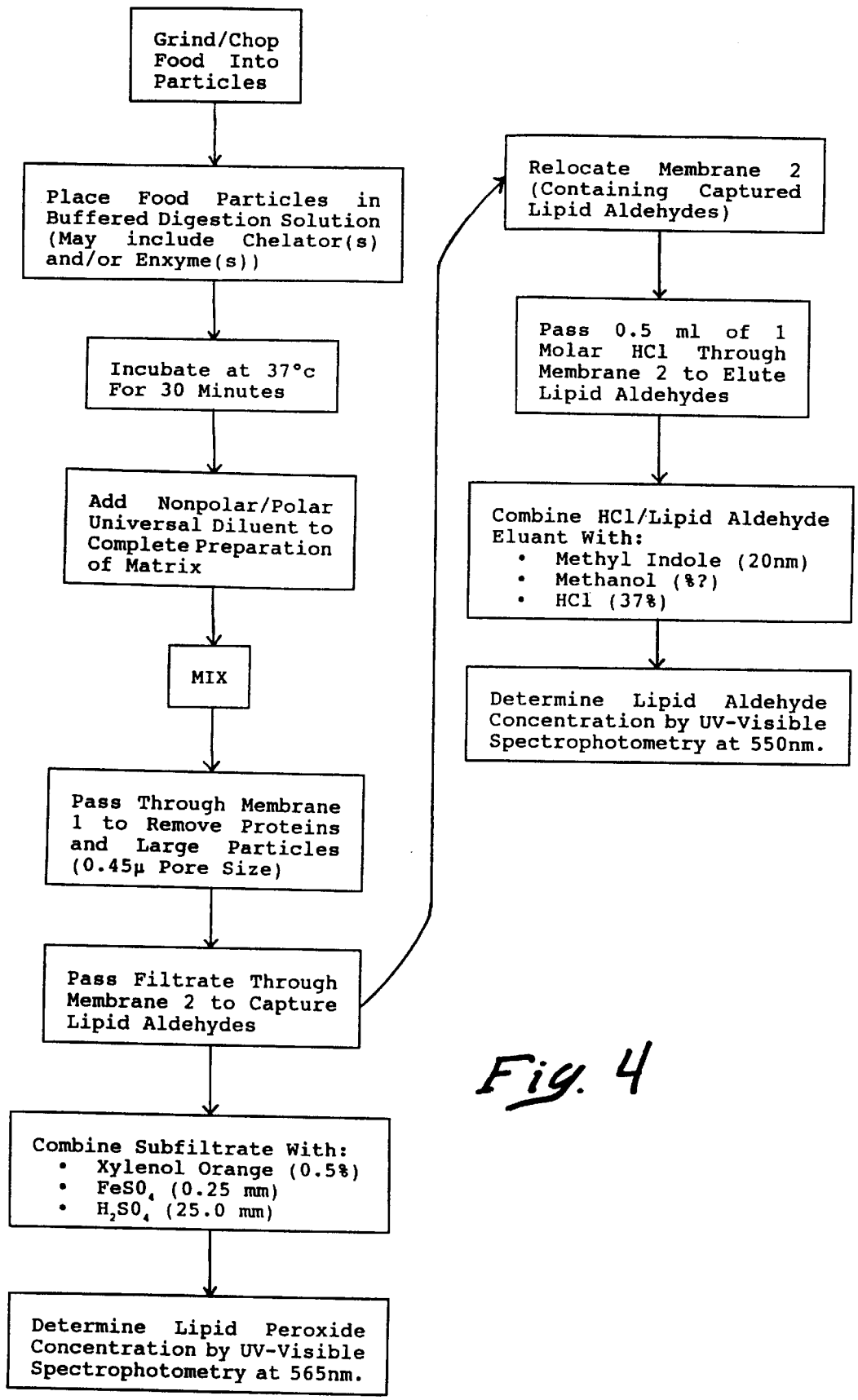
FIG. 4 is a flow diagram of a specific method of present invention which is usable for determining the concentrations of a) lipid hydroperoxides and b) malonaldehyde in a food, as a means of assessing rancidity or antioxidant status of the food.

FIG. 4 is a flow diagram showing an example of a method of the present invention wherein lipid peroxides and lipid aldehydes are quantitatively determined in a food matrix. This method is usable to assess the degree of rancidity of fats within the food and/or the antioxidant status of the food, as described more fully herebelow.

Initially, the food is ground into particles or a mash in accordance with well-known techniques for preparation of food samples for analysis.

Thereafter, a buffered digestion solution containing one or more enzymes, such as lipase enzymes, is combined with the ground or chopped food matrix to digest and liquify at least the fatty portions thereof. This digestion solution may additionally include chelators, such as EDTA, to chelate substances which could interfere with subsequent analysis (e.g., EDTA will bind $Fe^{++}$ present in the matrix to prevent $Fe^{++}$ from acting as a proxidant). Additionally, such digestion solution may include one or more antioxidant(s) to prevent further oxidative degradation of the matrix during the analytical procedure. The ground or chopped food particles may be incubated in this buffered digestion solution at 37° C. for 30 minutes.

Thereafter, a non-polar/polar universal diluent, such as the isopropanol-butanol formulation described as Universal Diluent I hereabove or the cyclodextrin-$H_2O$ formulation described as Universal Diluent II hereabove, is added to the digested food matrix, and the resultant mixture is mixed by vortexing or other suitable mixing techniques, to complete preparation of the matrix sample. Thereafter, the prepared matrix sample containing the buffered digestion solution and non-polar/polar universal diluent is passed through the first membrane, which is a microporous membrane (e.g., mixed cellulose ester film having a pore size of 0.2–1.0 microns and preferably about 0.45 microns). The pore size of this first membrane will prevent large proteins and solid particles larger than the pore size, from passing through the membrane, while allowing a filtrate containing small food particles (e.g., less than the pores size) and the lipid peroxides and lipid aldehydes, to pass therethrough.

The filtrate which passed through the first membrane is subsequently passed through a second membrane, which is operative to capture the lipid aldehydes (e.g., malonaldehyde) contained within the filtrate, while allowing a sub-filtrate containing the lipid peroxidase to pass therethrough. One example of a second membrane which may be utilized to capture the lipid aldehydes in this manner is a cellulose film having a DEAE membrane covalently bound thereto and having pores of approximately 0.2 microns formed therein (e.g., NA-45, Schleicher & Schuell GmbH, P.O. Box 4, D37582, Dassel, Germany). Alternative types of membranes useable to capture lipid aldehydes in this embodiment are listed in the table of FIG. 6.

The sub-filtrate (containing lipid peroxides) which passes through the second membrane will be collected in a receiving well or other vessel, wherein such sub-filtrate is combined with a reagent mixture containing 0.5% xylenol orange, 0.25 millimoles $FeSO_4$ and 25.0 millimoles $H_2SO_4$. The xylenol orange reagent present in this mixture will undergo a color change (i.e., change from orange to blue color of varying shade) in relation to the concentration of lipid peroxides present in the sub-filtrate. Thus, the concentration of lipid peroxides present in the sub-filtrate may be determined colorimetrically, or more precisely by UV-visible spectrophotometry at 565 nm, in accordance with well known analytical methodology.

The second membrane, which contains the captured lipid aldehydes, is then repositioned adjacent a second receiving well or vessel and a flush solution, such as 0.5 ml of 1 M HCl, is passed through the second membrane to elute the lipid aldehydes therefrom. In this manner, an eluant comprising the HCl flush solution along with the eluated lipid aldehydes is received within the second receiving well or vessel.

A second reagent mixture, consisting of a 20 milimolar solution of methyl indole in methanol mixed with 37% HCl, at a volume ratio of 1.3 (methyl indole) to 0.4 (HCl) is then combined with the eluant in the second receiving well to form a reagent-eluant admixture. The methyl indole contained in this second eluant mixture will undergo a color change to increasingly darker shades of pink or red in relation to increasingly high concentrations of lipid aldehydes present in the reagent-eluant admixture.

In this regard, the concentration of lipid aldehydes present in the reagent-eluant admixture may be determined calorimetrically, or more precisely by UV-visible spectrophotometry at 550 nm, in accordance with well-known analytical methodology.

It will be appreciated that the particular example shown in FIG. 4 is only one of many ways in which the method and system of the present invention may be adapted to determine lipid aldehydes and lipid peroxides in a food matrix. Various modifications or alterations may be made to the example shown in FIG. 4, without departing from the intended spirit and scope of the invention. For example, in some instances it may be desirable for the second membrane to capture lipid peroxides, rather than lipid aldehydes. Example of membranes which may be substituted for capturing lipid peroxides in this embodiment of the invention include polyamide film membranes having pores of approximately 0.1–0.45 microns, and preferably between 0.1–0.2 microns (e.g., Nytrons, Schleicher & Schuell, GmbH, P.O. Box 4, D37582, Dassel, Germany) or a polypropylene matrix membrane having hydrophobic affinity (e.g., Product No. Selex 20, Schleicher & Schuell GmbH, P.O. Box 4, D37582, Dassel, Germany), or a silica fused glass fiber membrane (e.g., Product No. GF25, Schleicher & Schuell, GmbH, P.O. Box 4, D37582, Dassel, Germany). In such embodiments wherein the second membrane is utilized to capture lipid peroxidases rather than lipid aldehydes, the methyl indole/methanol HCl reagent mixture will be added to the first retaining well or vessel, rather than the second retaining well or vessel so as to accomplish analysis of the lipid aldehydes which are received in the first retaining well. Conversely, the xylenol orange/$FeSO_4$/$H_2SO_4$ reagent will be added to the second retaining well or vessel rather than the first retaining well or vessel, so as to analyze the lipid peroxides present in the second retaining well in this modified embodiment.

Moreover, this method for determining lipid peroxides and lipid aldehydes in foods may be further modified to assess the antioxidant status of foods by adding one or more antioxidant chemicals to the food matrix prior to preparation thereof. Additionally, in such embodiments of this method wherein it is desired to assess the antioxidant status of the food, an oxidation accelerating step such as adding an oxidation accelerating chemical, exposing to high intensity light or periods of heating, such as heating to 60° for 15 minute increments, will be utilized to oxidatively challenge the food matrix, thereby facilitating an assessment of the efficacy of the antioxidant additives contained within the food matrix. (i.e., sufficient levels of antioxidant additives will prevent lipid peroxide and/or lipid aldehyde formation while insufficient levels of antioxidants will allow lipid peroxide and/or lipid aldehydes to form as the result of oxidative degradation of fats or oils. The time to rapid increase of oxidation is directly related to shelf life.

v. Adaptations of the Invention for Various Specific Analytes

FIG. 5 is a table which summarizes numerous adaptations of the methodology of the present invention, to permit analysis of various different analytes in various different types of matrices. The following written descriptions are provided to further summarize each of the different adaptations shown in FIG. 5:

a. Lipid Peroxides/Lipid Aldehydes in Fatty Foods/Oils

The first horizontal column of FIG. 5 describes an alternative method of the present invention for determining a) lipid peroxides and b) lipid aldehydes in fatty foods or oils. In this embodiment, the first membrane is microporous mixed cellulose ester film having pores of approximately 0.45 microns formed therein. (e.g., Product No. ME-25, Schleicher & Schuell, GmbH, P.O. Box 4, D37582, Dassel, Germany) This first membrane removes proteins and/or particles which are greater in size than the 0.45 micron pore diameter, while allowing a filtrate containing the lipid peroxides and lipid aldehydes to pass therethrough.

The second membrane $M_2$ of this embodiment comprises polyamide film having pores of approximately 0.2 microns formed therein (Nytran S, Schleicher & Schuell, GmbH, P.O. Box 4, D37582, Dassel, Germany). This second membrane operates to bind and hold the lipid aldehydes, while allowing a sub-filtrate containing the lipid peroxides to pass therethrough.

The first reagent $R_1$, which is combined with the first filtrate containing the lipid peroxides, comprises xylenol orange. The xylenol orange will undergo a color change in relation to the concentration of lipid peroxides present in the first filtrate, and may be assessed visually, calorimetrically or spectrophotometrically in accordance with well known laboratory methods.

The second reagent $R_2$, which is combined with an eluant from membrane to $M_2$ containing the captured lipid aldehydes, comprises methyl indole. The methyl indole will undergo a color change in relation to the concentration of lipid aldehydes present in the eluant. The concentration of lipid aldehydes present in the eluant may then be determined visually, calorimetrically or by spectrophotometric measurement in accordance with well known laboratory methods.

b. Lipid Peroxides and Hexanal in Peanuts or Peanut Paste

The second horizontal line of the table describes an embodiment of the present invention wherein a) lipid peroxides and b) hexanal are determined in peanuts or peanut paste. In this embodiment, the first membrane $M_1$ is microporous cellulose ester membrane having pores of approximately 0.45 microns (e.g., type ME 25, Schleicher & Schuell, GmbH, P.O. Box 4, D37582, Dassel Germany) which is operative to remove proteins are particulate matter larger than 0.45 microns, while allowing a filtrate containing lipid peroxides and hexanal to pass therethrough.

The second membrane $M_2$ in this embodiment is operative to capture peroxides while allowing a sub-filtrate containing hexanal to pass therethrough. One example of a membrane of this type is silica glass having pores of 0.2–0.45 microns formed therein, such that the silica coating of the membrane will bond and hold lipid peroxidases. Such silica glass membrane is available commercially as Product No. GF-25 Membrane, Schleicher & Schuell, GmbH, P.O. Box 4, D37582, Dassel Germany.

The first reagent $R_1$ in this embodiment is a mixture of methyl indole and methane sulfonic acid. This first reagent $R_1$ is combined with the hexanal containing sub-filtrate which has passed through membranes $M_1$ and $M_2$, and undergoes a color change in relation to the concentration of hexanal present in such sub-filtrate. In this manner, the concentration of hexanal in the sub-filtrate may be determined visually, colorametrically or more precisely by UV-visible spectrophotometry utilizing well-known laboratory techniques.

The second reagent in this embodiment comprises xylenol orange for lipid peroxides. This xylenol orange reagent, when combined with lipid peroxide containing eluant from the second membrane $M_2$ will undergo a color change in relation to the concentration of lipid peroxides present is such eluant. Thereafter, the concentration of lipid peroxides present may be determined visually, colorametrically, or more precisely by UV-visible spectrophotometry in accordance with well-known laboratory techniques.

In this manner, this embodiment of the present invention enables one to determine the relative presence and/or concentrations of lipid peroxides and hexanal in peanuts or peanut paste as means for assessing the oxidative degradation and/or antioxidant status of such foods.

c. Lipid Peroxides, Malonaldehyde and Histamine in Fish

The third horizontal column of FIG. 5 describes an embodiment of the invention wherein a) lipid peroxides, b) malonaldehyde and c) hexanal are determined in fish.

In this embodiment, the first membrane $M_1$ may be formed of mixed cellulose ester film having pores of approximately 0.45 microns (e.g., Product ME-25, Schleicher & Schuell GmbH, P.O. Box 4, D37582, Dassel, Germany), as described hereabove.

The second membrane $M_2$ is a DEAE cellulose (diethylaminoethyl-$OC_2H_4N(C_2H_5)2$), membrane which will capture malonaldehyde while allowing a sub-filtrate containing lipid peroxides and hexanal to pass therethrough.

The third membrane $M_3$ in this embodiment is silica glass having pore sizes 0.2–0.45 microns as described hereabove, for capturing lipid peroxides while allowing a sub-sub-filtrate containing histamine to pass therethrough.

The first reagent $R_1$ in this embodiment is a mixture of histaminase and peroxidase, for determining histamine in the sub-sub-filtrate which as passed through membranes $M_1$, $M_2$, and $M_3$. Histamine contained within the sub-sub-filtrate is initially broken down by the histaminase, into aldehyde, amine and peroxide molecules. The peroxide break-down product of the histamine undergoes a color-forming coupling reaction with the peroxidase present in the histaminase/peroxidase mixture, thereby providing a colored reaction product wherein the histamine concentration may be determined visually, colorametrically, or more precisely by UV-visible spectrophotometry, in accordance with well-known laboratory methods.

The second reagent $R_2$ in this embodiment comprises methyl indole which is combined with malonaldehyde containing eluant from the second membrane $M_2$. The methyl indole will undergo a color change in relation to the concentration of malonaldehyde present in such eluant and, thus, will permit the concentration of malonaldehyde to be determined visually, colorametrically or more precisely by UV-visible spectrophotometry in accordance with well-known laboratory methods.

The third reagent $R_3$ in this embodiment comprises xylenol orange and is combined with the eluant from the third membrane $M_3$ containing lipid peroxides. The xylenol orange will undergo a color change in relation to the concentration of lipid peroxides present in such eluant. In this manner, the concentration of lipid peroxides may be determined visually, colorametrically or more precisely by UV-visible spectrophotometry in accordance with well-known laboratory methods.

d. Lipid Peroxides and Conjugated Linoleic Acid in Dairy Products

The fourth horizontal column of FIG. 5 describes an embodiment of the invention wherein a) lipid peroxides and b) conjugated linoleic acid are determined in dairy products.

In this embodiment, the first membrane $M_1$ is microporous cellulose acetate having pores of approximately 0.45 microns formed therein (e.g., ME-25, Schleicher & Schuell GmbH, P.O. Box 4, D37582, Dassel, Germany). This microporous nylon membrane will serve to prevent proteins and particles larger than 0.45 microns from passing therethrough, while permitting a filtrate containing lipid peroxide and conjugated linoleic acid to pass therethrough.

The second membrane $M_2$ of this embodiment is a nitrocellulose film membrane coated with antibody to conjugated linoleic acid to capture and hold conjugated linoleic acid while allowing a sub-filtrate containing lipid peroxides to pass therethrough. Such nitrocellulose membrane coated with antibodies to conjugated linoleic acid is prepared by impregnating or coating glutaraldehyde-conjugated antibodies to linoleic acid upon nitrocellulose film membrane in accordance with known methodology. Palfree, R., and Elliot, B., see, J. Immunol. Meth. 52 393–408 (1982).

The first reagent $R_1$ is xylenol orange for determination of the concentration of lipid peroxides in the sub-filtrate which has passed through the first and second membranes $M_1$ and $M_2$. As described hereabove, the xylenol orange reagent will undergo a color change in relation to the concentration of lipid peroxides present in the filtrate and, accordingly, such concentration of lipid peroxides may be determined visually, colorametrically, or by UV-visible spectrophotometry in accordance with well-known laboratory techniques.

The second reagent $R_2$ in this embodiment is fat red dye, which facilities determination of conjugated linoleic acids by enzyme immunoassay. The conjugated linoleic acid contained within the second membrane $M_2$ is eluded by way of a flush solution in to a second receiving well and is combined with the fat red dye reagent. Thereafter the eluant-fat red dye reagent combination is subjected to enzyme immunoassay to determine the concentration of conjugated linoleic acid present therewithin.

In this manner, the method of the present invention provides for relatively simple determination of lipid peroxidase and conjugated linoleic acid concentrations in dairy products or other foods.

e. Lipid Peroxides and Cholesterol Oxides in Foods

The fifth horizontal column of FIG. 5 describes an embodiment of the present invention wherein a) lipid peroxides and b) cholesterol oxides are determined in foods.

In this embodiment, the first membrane $M_1$ is microporous nylon having pores of approximately 0.45 microns to prevent proteins and particles larger than 0.45 microns from passing therethrough, while allowing a filtrate containing lipid peroxides and cholesterol oxides to pass therethrough.

The second membrane $M_2$ in this embodiment is a nitrocellulose film coated with antibody to cholesterol oxide, and is operative to capture and hold cholesterol oxide while allowing a sub-filtrate containing lipid peroxides to pass therethrough.

The first reagent $R_1$ comprises xylenol orange for determination of lipid peroxides. The xylenol orange reagent will undergo a color reaction in relation to the concentration lipid peroxides present in the filtrate which has passed through the first and second membranes $M_1$ and $M_2$. Such filtrate-xylenol orange admixture may then be assessed visually, colorametrically or more precisely by UV-visible spectrophotometry in accordance with well-known laboratory techniques, to determine the presence and/or concentration of lipid peroxides in the filtrate.

The second reagent $R_2$ in this embodiment is 10% N,N-dimethyl phenylene diamine, which is combined with cholesterol oxide containing eluant from the second membrane $M_2$ to provide an eluant N,N-dimethyl phenylene diamine admixture within which the presence or concentration of cholesterol oxide may be determined by enzyme immunoassay, in accordance with well-known laboratory techniques.

f. Sulfites, Free Aldehydes and Sulfite-Bound Aldehydes in Beer or Wine

The sixth horizontal column on the table of FIG. 5 describes an embodiment of the present invention wherein a) sulfites, b) free aldehydes, and c) sulfite-bound aldehydes are determined in beer or wine.

In this embodiment of the method, the first membrane $M_1$ is a mixed cellulose ester film having pores of approximately 0.45 microns formed therein (e.g., Product No. ME-25, Schleicher & Schuell GmbH, P.O. Box 4, D37582, Dassel, Germany) as described hereabove. This first membrane $M_1$ prevents proteins and particles larger than 0.45 microns from passing therethrough, while allowing a filtrate containing sulfites, free aldehydes and sulfite-bound aldehydes to pass therethrough in a filtrate.

The second membrane $M_2$ in this embodiment may be formed of DEAE cellulose (diethylaminoethyl-$OC_2H_4N$ $(C_2H_5)_2$) such as, Product No. NA45, Schleicher & Schuell, GmbH, P.O. Box 4, D37582, Dassel, Germany. This DEAE cellulose membrane operates to capture sulfites and sulfite-bound aldehydes, while allowing a sub-filtrate containing free aldehydes to pass therethrough such that such sub-filtrate may be collected in a first receiving well or vessel.

The first reagent $R_1$ in this embodiment comprises methyl indole, and is combined with the filtrate in the first receiving well such that the methyl indole reagent will undergo a color-change in accordance with concentration of free aldehydes present in the filtrate. In this manner, the filtrate-methyl indole admixture may be analyzed visually, colorametrically or, more precisely, by UV-visible spectrophotometry to determine the presence or concentration of free aldehydes in the filtrate.

The second reagent $R_2$ in this embodiment is sulfite oxidase. The sulfite oxidase is initially combined with an eluant from the second membrane $M_2$ at an acidic pH at which the concentration of free sulfites in the eluant-sulfite oxidase admixture may be determined by UV-visible spectrophotometry in accordance with well-known laboratory techniques. Thereafter, the pH of the $M_2$ eluant-sulfite oxidase admixture is adjusted to an alkaline pH whereby the concentration of sulfites bound to aldehydes within such admixture may be determined by UV-visible spectrophotometry in accordance with well-known laboratory techniques. Thus, the relative concentration of free and complexed sulfites in the eluant from the second membrane $M_2$ are determined using the same reagent (sulfite oxidase) by modifying the pH of the admixture.

g. Sulfites and Bromates in Beer, Wine or Bread

The seventh horizontal column of FIG. 5 describes an embodiment of the present invention wherein sulfites and bromates are determined in beer, wine or bread.

In this embodiment, the first membrane may comprise microporous polycarbonate film (e.g., Isopore HTTP, Millipore Corporation, 80 Ashby Rd., Bedford, Mass.). This polycarbonate film membrane prevents some of the oxidizing aldehydes and carbonyls from passing therethrough, while allowing a filtrate containing sulfite and bromates present within the matrix, to pass therethrough.

The second membrane $M_2$ in this embodiment may be formed of polyamide film capable of capturing organohalides (e.g., bromates), while allowing a sub-filtrate containing sulfites to pass therethrough. One commercially available polyamide film membrane which is usable for this application is a polyamide film membrane (e.g., type NL, Schleicher & Schuell, GmbH, P.O. Box 4, 237582, Dassel, Germany).

The first reagent $R_1$ in this embodiment is sulfite oxidase, and is combined with the sub-filtrate which has passed through the first and second membranes $M_1$ and $M_2$ to provide a sub-filtrate-sulfite oxidase add mixture from which the concentration of sulfites may be determined by the UV-visible spectrophotometry in accordance with well known laboratory methods.

A flush solution is used to elute the captured organohalides from the second membrane $M_2$ into a separate receiving well. The second reagent $R_2$ is a starch solution. Such starch solution is added to the eluant in the second receiving well. Thereafter, the eluant-starch solution add mixture contained in the second receiving well is titrated with iodine to determine the concentration of bromates therewithin. This technique is well known in the art, and is sometimes referred to as the "Bromine Clock" analysis.

h. Clenbuterol Residues in Meats

The eighth horizontal column of FIG. 5 describes an embodiment of the present invention wherein residues of clenbuterol are determined in meats. Clenbuterol is a beta-adrenergic agonist that is sometimes administered to animals (e.g. lambs) to accelerate weight gain. Excessive levels of clenbuterol in the animal meat are undesirable. Accordingly, measurement of clenbuterol concentrations in meats is sometimes required.

The first membrane $M_1$ in this embodiment may be formed of microporous nitrocellulose or mixed cellulose ester film which is free of Triton™ surfactant (e.g., Product No. TF 0.45, Milipore Corporation, 80 Ashby Rd., Bedford, Mass.) and operates to remove particles and other matter greater than the 0.45 micron membrane pore size, but which allows organic molecules such as herbicides and drugs to pass through the first membrane $M_1$ in a filtrate.

The second membrane $M_2$ in this embodiment is a nitrocellulose film coated with antibody to clenbuterol so as to capture and concentrate clenbuterol contained in the filtrate which has passed through the first membrane $M_1$. This second membrane $M_2$ may be prepared by impregnating or coating a nitrocellulose film membrane (e.g., Immobilon-$NC^{PURE}$ Transfer Membrane, Millipore Corporation, 80 Ashby Rd., Bedford, Mass.) with glutaraldehyde-conjugated clenbuterol in accordance with known methods.

In this embodiment, only a "second" reagent $R_2$ is utilized. Such second reagent $R_2$ is an enzyme which conjugates clenbuterol to facilitate determination of the clenbuterol concentration by enzyme immunoassay techniques well known in the art. In this regard, a flush solution such as a surfactant-containing salt solution (containing, 1 M NaCl w/10% TX-100 surfactant, (e.g., Triton™ surfactant) is utilized to elute the captured and concentrated clenbuterol from the second membrane $M_2$ and provides an eluant wherein clenbuterol is present at sufficient concentrations to be analyzed.

In this embodiment, only a second reagent $R_2$ is utilized. Such second reagent is an enzyme which conjugates clenbuterol so as to enable clenbuterol to be determined by well-known enzyme immunoassay techniques. In this manner, the second reagent $R_2$ is combined with the eluant from the second membrane $M_2$ to provide an eluant-enzyme add mixture from which the concentration of clenbuterol may be determined by enzyme immunoassay.

i. Ratio of Alachlor Herbicide to All Other Chloroacetamide Herbicides in Fruits or Vegetables The ninth horizontal column of the table of FIG. 5 describes an embodiment of the present invention the concentration of a specific chloroacetamide herbicide, known as alachlor, may be determined relative to the total concentration of all chloroacetamide herbicides contained within a fruit or vegetable matrix.

In this embodiment, the first membrane may comprise a nitrocellulose or mixed cellulose ester film which has pores of approximately 0.45 microns and which is free of Tritonm surfactant (e.g., Low Extractable HATF membrane, Millipore Corporation, 80 Ashby Rd., Bedford, Mass.) as described hereabove.

The second membrane $M_2$ is a nitrocellulose or polypropylene film coated with an antibody to alachlor such that alachlor passing therethrough will be captured within the second membrane and to while a filtrate containing all other chloroacetamide herbicides will be permitted to pass through the second membrane $M_2$.

The first and second reagents $R_1$ and $R_2$ both comprise ethylchloroformate, which will combine with alachlor and/or other chloroacetamide herbicides to permit the concentration of alachlor and/or other chloroacetamide herbicides to be performed by UV-visible spectrophotometry in accordance with well known laboratory techniques. Thus, the ethylchloroformate first reagent $R_1$ is added to the sub-filtrate which is passed through membranes $M_1$ and $M_2$ to determine the concentration of non-alachlor chloroacetamide herbicides contained within such sub-filtrate. Thereafter, the ethylchloroformate reagent $R_2$ is combined with an eluant from the second membrane $M_2$ to determine the concentration of alachlor herbicide within such eluant. In this manner, this method of the present invention provides a determination of the relative concentrations of alachlor and all other chloroacetamide herbicides within the fruit or vegetable matrix.

j. Mycotoxins of Fusarium $T_2$ and Zearalenone in Grains

The tenth horizontal column of the table of FIG. 5 describes an embodiment of the present invention wherein the concentrations of a) fusarium $T_2$ mycotoxin ($MT_2$) and zearalenone mycotoxin (ZE) are determined in grains.

The first membrane $M_1$ in this embodiment is microporous PVDF having pores of approximately 0.45 microns formed therein (Micropore 0.45, Milipore Corporation, 80 Ashby Rd., Bedford, Mass. 01730-2271) to prevent large proteins and particles greater than 0.45 microns from passing therethrough, while allowing a filtrate containing $MT_2$ and ZE to pass therethrough.

The second membrane $M_2$ in this embodiment is a PVDF film coated with an antibody to $FT_2$, such antibody being bound to the PVF membrane substrate by glutaraldehyde. This second membrane $M_2$ will capture the $FT_2$, while allowing the ZE to pass therethrough.

The third membrane $M_3$ in this embodiment is a PVDF film coated with antibody for ZE, such antibody being bound to the PVDF film substrate by glutaraldehyde. This third membrane $M_3$ operates to capture ZE.

The captures $FT_2$ is eluded from the second membrane $M_2$ into a first receiving well and the first reagent $R_1$ which comprises horseradish peroxidase and an antibody conjugate for $FT_2$ is combined therewith to provide a first eluant-reagent $R_1$ admixture from which the concentration of $FT_2$ may be determined by enzyme immunoassay techniques well known in the art.

The third membrane $M_3$ is eluded with a second reagent $R_2$ containing horse radish peroxidase and an antibody conjugate for ZE so as to provide a second eluant-second reagent $R_2$ admixture from which the concentration of ZE may be determined by enzyme immunoassay techniques, well known in the art.

k. Malonaldehyde, Lipid Peroxides and Xanthine in Fish, Beans or Coffee

The eleventh horizontal column of the table of FIG. 5 describes an embodiment of the present invention wherein a) malonaldehyde, b) lipid peroxides and c) xanthines are determined in fish, beans or coffee.

In this example, the first membrane $M_1$ is microporous PVDF having pores of 0.42 or 0.45 microns (e.g., Durapore 0.2 or 0.45, Milipore Corporation, 80 Ashby Rd., Bedford, Mass.) and operates to prevent large proteins or particles greater than the membrane pore size from passing therethrough, while allowing a filtrate containing malonaldehyde, lipid peroxides and xanthine to pass therethrough.

The second membrane $M_2$ in this embodiment operates to capture lipid peroxides, while allowing malonaldehyde and xanthine to pass therethrough. Such second membrane $M_2$ may comprise a polypropylene matrix with hydrophobic affinity or silica fused glass fiber.

The third membrane $M_3$ in this embodiment is operative to capture xanthines from the sub-filtrate which has passed through the second membrane $M_2$, while allowing a sub-sub-filtrate containing malonaldehyde to pass through the third membrane $M_3$ and into a first receiving well. Such third membrane $M_3$ may be formed of PVDF having xanthine oxidase bound thereto by glutaraldehyde.

In this embodiment, a first reagent $R_1$ is methyl indole which will react with malonaldehyde present in the sub-sub-filtrate which has passed through the first, second and third membranes $M_1$, $M_2$, $M_3$, to provide a reagent-sub-filtrate admixture from which the concentration of malonaldehyde may be determined in accordance with analytical methods well known in the art.

In this embodiment, the second reagent $R_2$ is xanthine oxidase which, when combined with the eluant from the second membrane $M_2$, will react with lipid peroxides present in such eluant to provide an eluant-reagent admixture from which the concentration of lipid peroxides may be determined by analytical methods well known in the art.

Also, in this embodiment, the third reagent $R_3$ is peroxidase which, when combined with eluant from the third membrane $M_3$, will react with the xanthine contained therein to provide a second eluant-reagent admixture from which the concentration of xanthine may be determined by determined by analytical methods well known in the art.

B. Apparatus of the Present Invention

FIGS. 6–11 show various types of test kits and apparatus which are usable to perform the above-described methods of the present invention.

The test kits of the present invention range in complexity from a relatively simple kit shown in FIGS. 1–1c for detection of a single analyte in a complex matrix, to multiple-membrane, multiple-cell test kit for determining two or more analytes in a multiplicity of sample matrices.

i. A Test Kit for Visual Determination of a Single Analyte

With reference to FIGS. 6–6c, the present invention provides a test kit which is usable to qualitatively determine, the presence of, or roughly quantify the concentration of, a single analyte in a matrix such as food, biological fluid.

This test kit 10 comprises a sample receiving vessel 12 having a top opening, a generally solid side wall, and a plurality of flow-through apertures 14 formed in the bottom wall thereof. The base of this sample receiving vessel 12 is seated within a retainer ring 16 having a membrane 18 having a membrane mounted therewithin, such that the flow through apertures 14 of the sample receiving vessel 12 are juxtapositioned with the upper surface of the membrane 18.

The retaining ring 16 and membrane 18 are mounted upon a receiving well 20 having a reagent-containing pad 22 positioned therewithin.

A color chart 24 is provided along with the test kit, and shows different colors or different shades of colors to which the reagent-containing pad 22 will turn when wetted or soaked with differing concentrations of the analyte.

In operation, the prepared matrix 15 is deposited into the sample receiving vessel 12. Such prepared matrix 15 may comprise chopped or ground solid material (e.g., solid foods) or a flavorable liquid (e.g., oils) combined with any desired solvents, digestants, enzymes, chelators, additives (e.g., antioxidants) or other components necessary or desirable in connection with the intended analysis.

The prepared matrix 15 deposited within the sample receiving vessel 12 will then percolate or flow downwardly through apertures 14 and through the membrane 16 into the receiving well 20 in contact with the reagent-containing pad 22.

The membrane 18 may be any suitable type of membrane operative to mechanically eliminate or filter out proteins, particles or matter exceeding a desired size, or may be adapted to chemically or biologically bind and hold certain materials to prevent such certain materials from passing into the receiving well 20. In this manner, the membrane 18 functions to further prepare the prepared matrix 15 for the desired reaction with the reagent contained in the reagent-containing pad 22.

After the reagent impregnated pad 22 has become wetted or soaked with the filtrate which has passed through the filter 18, the receiving well 20 may be detached and removed from the remainder of the test kit, so as to enable the operator to clearly view the upper surface of the reagent-impregnated pad 22 to compare the color of the pad 22 to the various colors shown on the color chart 24. In this manner, the operator may visually assess and determine the concentration of analyte which was present in the prepared matrix 15.

Paragraph it will be appreciated that in the test kit of this embodiment, and in all other embodiments described herein, the desired passage of the prepared matrix, filtrate, subfiltrate(s) or eluant(s) through the membrane(s) and/or other portions of the test apparatus may be accomplished by simple gravity feed, or may be assisted by any suitable means including but not limited to the application of positive pressure to drive the materials through the test apparatus, or negative pressure to pull such materials through the test apparatus.

EXAMPLE

A Test Kit For Determining When Cooking Oil Should be Changed

One particular application of the test kit 10 which may be manufactured and used in accordance with FIGS. 6–6c, is for testing of cooking oil (e.g., the type of oil used in commercial deep fryers) to determine whether such cooking oil is in need of change due to oxidative degradation.

Cooking oils, when heated, tend to degrade oxidatively. Therefore, a rapid simple color test for determining whether cooking oil has oxidatively degraded to point where it is desirable to change such cooking oil, could be used in the food service industry.

To provide a simple test kit for determining whether cooking is in need of change, the receiving vessel 12 may be pre-filled with a measured quantity of a solution of 0.5% cyclodextrin in 10% HCl. Thereafter, a prescribed volume of cooking oil may be added to the cyclodextin/HCl solution contained within the receiving vessel 12, and the vessel 12 may be manually shaken or mixed to provide a cooking oil/cyclodextran/HCl solution within the receiving vessel 12. Thereafter, the cooking oil/cyclodextrin/HCl solution contained within the receiving vessel 12 will pass downwardly through apertures 14 and will subsequently filter through the membrane 18. In this application, the membrane may be formed of mixed cellulose ester or nitrocellulose film having pores preferably of approximately 0.45 μm pore size, to remove particles of food and proteins in excess of the membrane pores size (e.g., 0.45 μm), while allowing a filtrate which contains the cooking oil/cyclodextrin/HCl mixture to pass downwardly into the receiving well 20 such that it saturates or contacts the reagent-containing pad 22 positioned therewithin.

In this application, the reagent containing pad 22 may be prepared by saturating a quantity of filter paper with a methyl indole/methanol solution, and subsequently allowing such solution to dry, thereby causing the filter paper to become coated or impregnated with methyl indole. Lipid aldehydes contained in the filtrate which saturates the reagent-containing pad 22 will subsequently react with the methyl indole on the pad 22 to produce a color change reaction.

After several minutes at room temperature, the resultant color change of the reagent-containing pad may be compared to the color chart 24, to determine whether the concentration of lipid aldehydes present in the cooking oil sample is high enough to indicate a need for change of the cooking oil. In this application, the lighter color shades indicated by numbers 1–3 of the color chart 24 shown in FIG. 6c may range from clear to medium blue, indicating acceptable concentrations of lipid aldehydes in the cooking oil sample, while the darker shades indicated by numbers 4–5 of the color chart 24 shown in FIG. 6c will be dark or deep blue, indicating unacceptably high concentrations of lipid aldehydes in the cooking oil and thereby notifying the user of a need for change of the cooking oil.

Thus, in accordance with the above-set-forth example, this embodiment of the present invention may be used for periodic (e.g., daily) checking of the cooking oil in restaurants, cafeterias, or other food preparation facilities, by a minimally trained person, to determine whether the cooking oil is presently in need of change.

ii. A Test Kit for Accurate Quantitative Determination of a Single Analyte in a Complex Matrix FIGS. 7a and 7b show an alternative embodiment 10a of a single-analyte test kit 10 shown in FIGS. 6–6c.

With reference to FIGS. 7a and 7b this embodiment of the single-analyte test kit 10a differs from the single analyte test kit 10 shown in FIGS. 6–6c in that it's sample receiving well 20a contains a liquid reagent or reagent mixture 24, rather than a reagent-containing pad 22.

In this embodiment, the filtrate which passes through the filter 18 is received within a pool of liquid reagent or reagent mixture 24 contained within the receiving well 20a.

Thereafter, the receiving well 20a wherein the reagent-filtrate admixture is contained may be inserted into an analytical instrument 26 or otherwise subjected to a chemical analysis or reading which is operative to quantitatively determine the concentration of analyte in the liquid mixture contained within the receiving well 20a. Any analytical instrument 26 used may be of any suitable type to perform the desired analysis, including but not necessarily limited to UV-visible spectrophotometers, pH meters, scintillation counters, calorimeters, gas chromatographs, other spectrophotometers, fluorometers, luminometers, photodiodes, optical sensors and/or electronic sensors.

iii. Test Kit For Determining Multiple Analytes

Figure 8A:
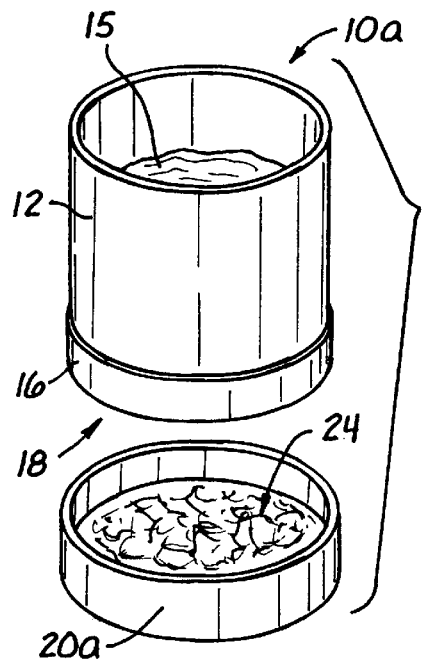
FIG. 8a is an exploded, perspective view of an apparatus of the present invention for detection of a single analyte in multiple samples.
Figure 8B:
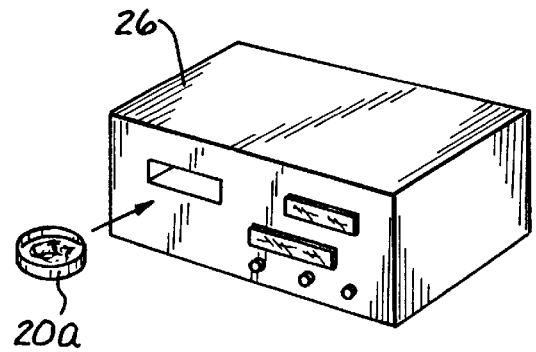
FIG. 8b is a perspective of an analytical instrument wherein the reagent-containing well portion of the apparatus shown in FIG. 8a may be inserted for analysis of or more analytes contained therein.

FIGS. 8a–8b show a modification of the test kits 10, 10a shown in FIGS. 6–6c and 7a–7b, usable to determine multiple (i.e., 2 or more) analytes wherein the modified test kit 10b is provided with a first retainer ring 16a having the first membrane 18a disposed therewithin and a second retainer ring 16b having a second membrane 18b disposed therewithin. As described hereabove with respect to the methodology of the invention, the second membrane 18b is operative to capture and hold one or more analytes, while allowing a sub-filtrate to pass therethrough into the receiving well 20a wherein a first reagent or reagent mixture 24a is contained. Such sub-filtrate passing into the receiving well 20a may contain one or more additional analytes which were not captured by the second membrane 18b.

Thereafter, the second retaining ring 16b having the second membrane 18b disposed therewithin is positioned adjacent or over top of a second receiving well 20b having a second reagent or reagent mixture 24b contained therewithin. A quantity of flush solution 28 is then passed through the second membrane 18b to elute the desired analyte(s) from the second membrane 18b such that an eluant 29 containing the analyte(s) from the second membrane 18b will be received within the second receiving well 20b and will mix with the second reagent or second reagent mixture 24b.

The first receiving well 24a having the first reagent or reagent mixture 24a and first analyte contained therein may subsequently be visually assessed or may be analyzed by the above-described analytical instrument(s) 26 to provide a determination or quantification of the concentration of the first analyte contained within the first receiving well 20a.

Thereafter, the second receiving well 20b may be visually assessed or analyzed by way of the analytical instrument(s) 26 to determine or quantify the concentration of second reagent contained within the second receiving well 20b.

iv. Apparatus for Concurrent Testing of a Multiplicity of Individual Samples

Figure 9A:
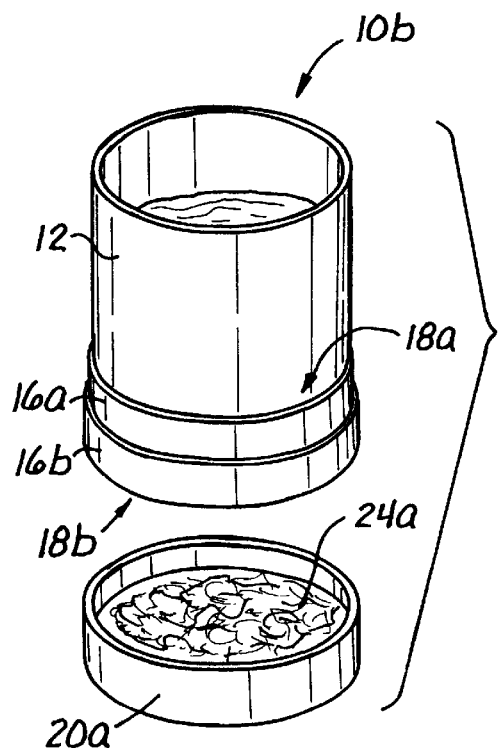
FIG. 9a is an exploded perspective view of an apparatus of the present invention for detection of multiple analytes in multiple samples.
Figure 9B:
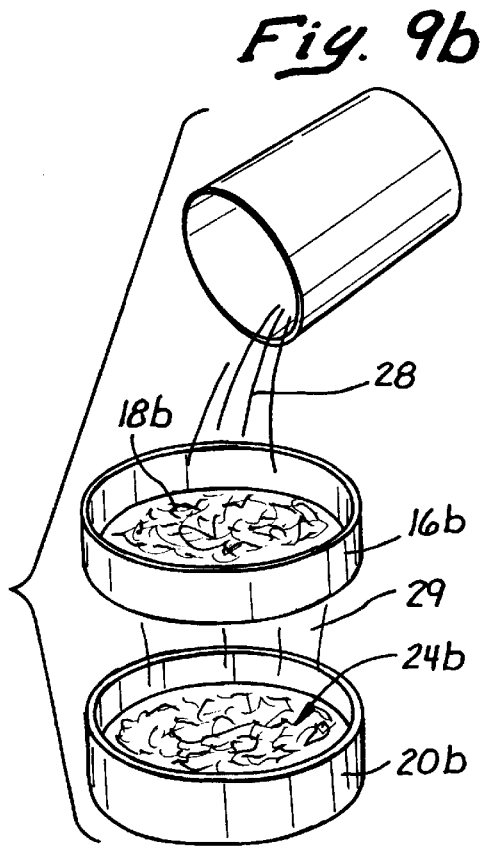
FIG. 9b is a perspective view of the second membrane portion of the apparatus shown in FIG. 9a positioned in relation to a second reagent-containing well such that an eluant from the second membrane may be passed into the second reagent-containing well for analysis of an analyte which had been captured in the second membrane.

Referring to FIG. 9, an embodiment of the test kit 10c which is adapted for determining the presence of a single analyte, in multiple samples. This embodiment of the test kit 10c comprises a sample receiving well tray 120 having numerous individual sample receiving wells 122 formed therein. Drain holes or openings (not shown) are formed in the floors of the individual sample-receiving wells 122, and such drain holes or openings may be initially closed off or covered by a removable layer of plastic film applied to the underside of the receiving well tray 120.

The receiving well tray 120 is insertable and nestable within a filter tray 160. The filter tray 160 has a plurality of filtration channels 162 formed therein. Such filtration channels 162 are sized and positioned to received therewithin the individual sample-receiving vessels 122 of the receiving vessel tray 120. First filters 180 are positioned transversely within each of the filtration channels 162 such that material which drains downwardly from the individual sample-receiving vessels 122 will pass through such filters.

The filter tray 160 is receivable and nestable within a receiving-well base 200. The receiving well base 200 comprises numerous individual reagent-containing receiving wells 202. The individual reagent-containing wells 202 are sized and positioned to receive therewithin the basal portions of the individual filtration channels 162. In this manner, filtrate which passes through the filters 180 positioned within each filtration channel 162 will subsequently flow downwardly into each reagent-containing well 202, wherein such filtrate will become mixed with the reagent contained therein to provide a desired filtrate-reagent admixture.

The reagent well base 120 of this embodiment is configured such that the combined receiving-vessel tray 120 and filter tray 160 will fit within and abut against a perimeter notch 204 so as to substantially seal thereagainst. The interiors of the reagent-containing wells 202 are in fluidic communication with a vacuum fitting 206 such that, when negative pressure is applied to the vacuum fitting 206, negative pressure will be created within reagent-containing wells 202 so as to draw or pull matter downwardly through the outlet openings of the receiving vessel tray 120 and through the filters 180 disposed within the filter tray 160. It will be appreciated, that as an alternative to the application of negative pressure to vacuum fitting 206, a positive pressure canopy or hood could be positioned over top of the receiving-vessel tray 120 in a manner which would apply positive pressure to the interior of the receiving-vessels 122, thereby driving or pushing matter downwardly through outlet openings in the receiving-vessel tray 120 and filters 180 in the filter tray 160.

Figures 10, 11:
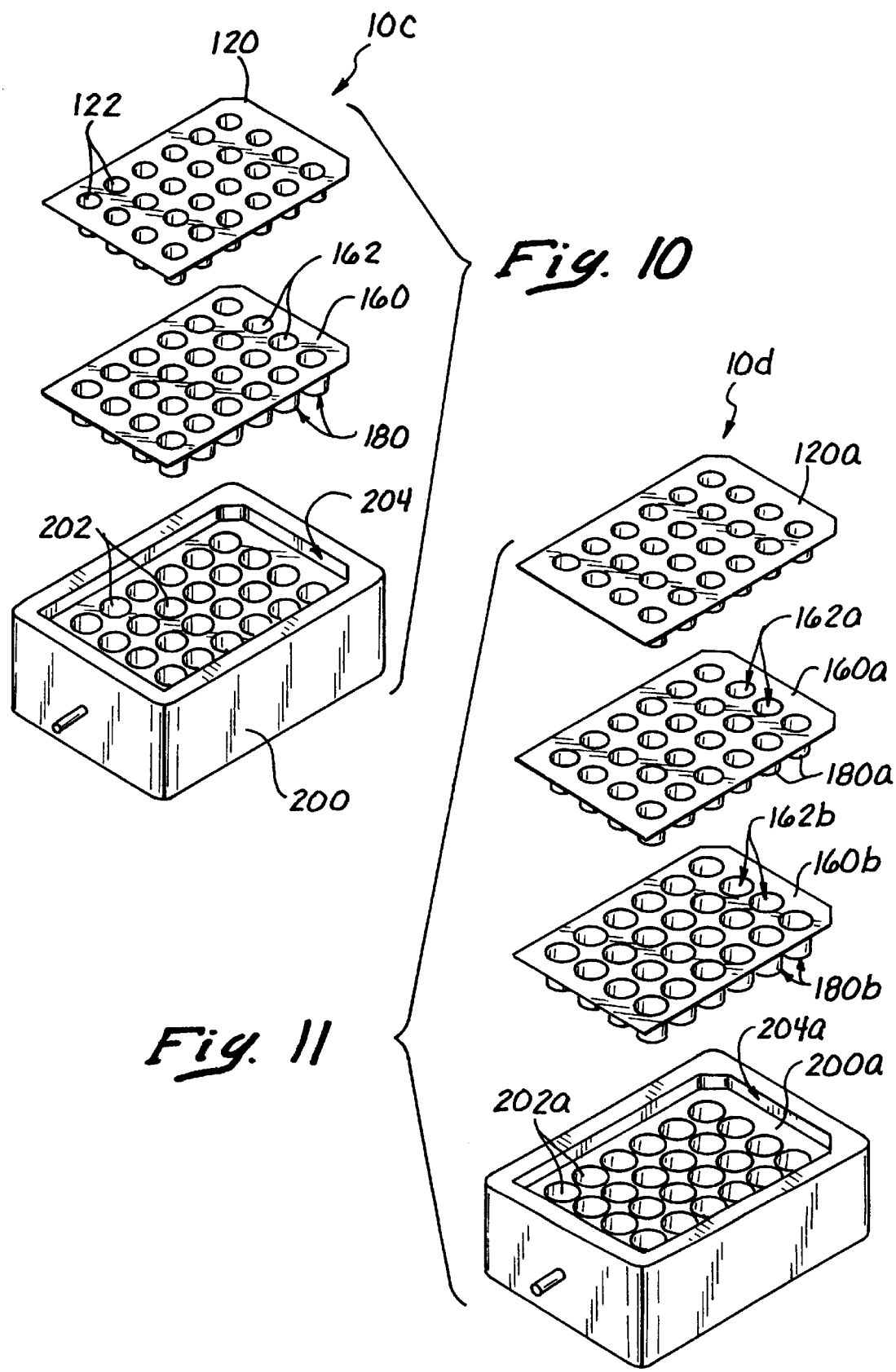
FIG. 10 is a partial perspective view of an apparatus of the present invention for detection of multiple analytes in multiple samples, showing a presently preferred mode of construction therefore.
FIG. 11 shows an apparatus for the determination of two separate analytes in a sample.

FIG. 10 shows another multiple-sample test kit 10d which is adapted for determination of two (2) analytes in each sample. With reference to FIG. 10, there is provided a test kit apparatus 10d which comprises a receiving-vessel tray 120a, a first filter tray 160a, a second filter tray 160b and a reagent well base 200a. In this embodiment, the individual filtration channels 162a of the first filter tray 160a contained first filters 180a, and the individual filtration channels 162b of the second filter tray 160b contain second filters 180b. The individual receiving vessels of the receiving vessel tray 120a are received downwardly within the individual filtration channels 162a of the first filter tray 160a are received downwardly within the individual filtration channels 162b of the second filtration tray 160b. Also, the individual filtration channels 162b of the second filtration 160b are received within the individual reagent wells 202a of the reagent well base 200a such that sealing contact is maintained about the outer peripheries of receiving vessel tray 120a, first filter tray 160a, second filter tray 160b and the outer perimeter 204a of the reagent well base 200a. As described hereabove with reference to FIG. 10, a negative pressure or vacuum source may be applied to the vacuum fitting 206 to draw matter downwardly through the first filters 180a, second filters 180b, and into the reagent-containing wells 202a of the reagent well base 200a. Thereafter, the second filter tray 160b may be removed from the assembly and the individual filter channels 162b of such second filter tray 160b may be combined with a different set of reagent wells 202a within the same or different reagent well base 200a and a desired eluant may be added to the individual filtration channels 162b of the second filter tray 160b to elute a desired second analyte which has been captured in the second filters 180b into the second or different individual reagent wells 202a.

In this manner, the modified embodiment shown in FIG. 11 is usable to determine two (2) separate analytes in each individual sample. It will be appreciated that, numerous additional individual analytes may be determined by adding more filtration trays in addition to the first filtration tray 160a and second filtration tray 160b shown in the embodiment of FIG. 11. This is in accordance with the above-described methodology of the present invention.

v. Preferred Construction of the Multiple-Sample Test Kits

Figure 12:
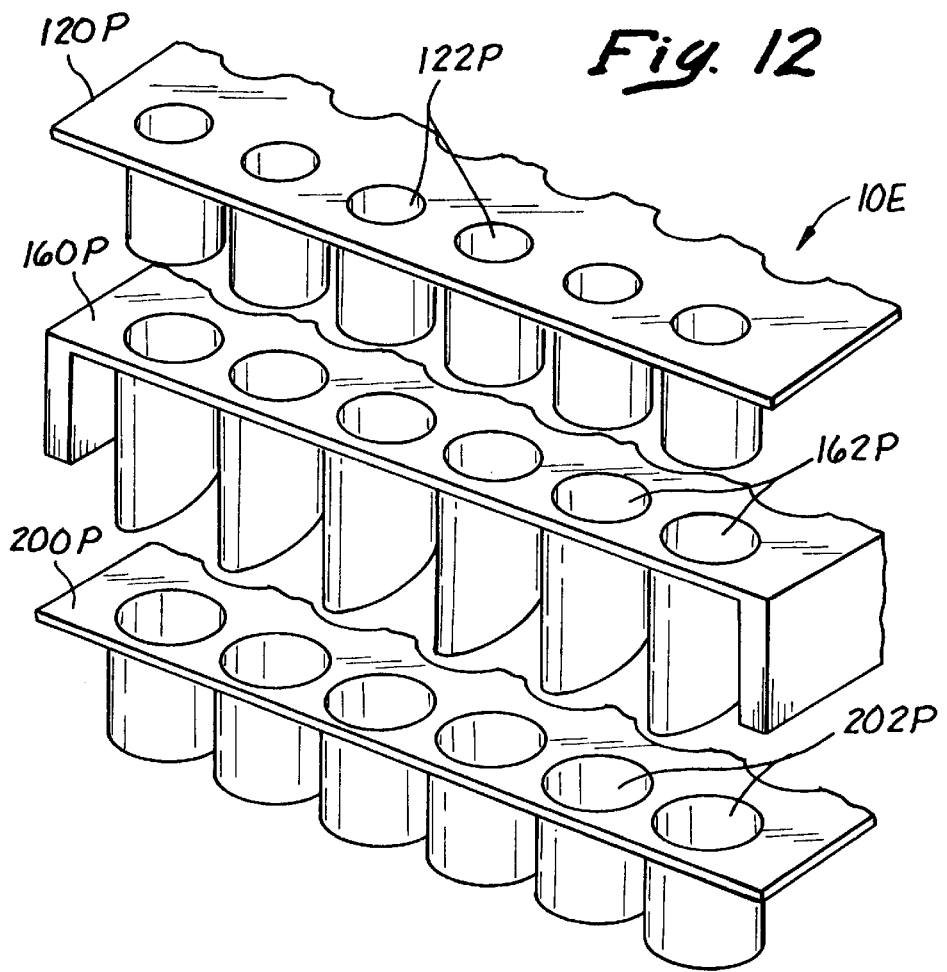
FIGS. 12 and 12a show a preferred type of construction which may be utilized for multiple-sample test kits of the type shown in FIGS. 10 and 11.
Figure 12A:
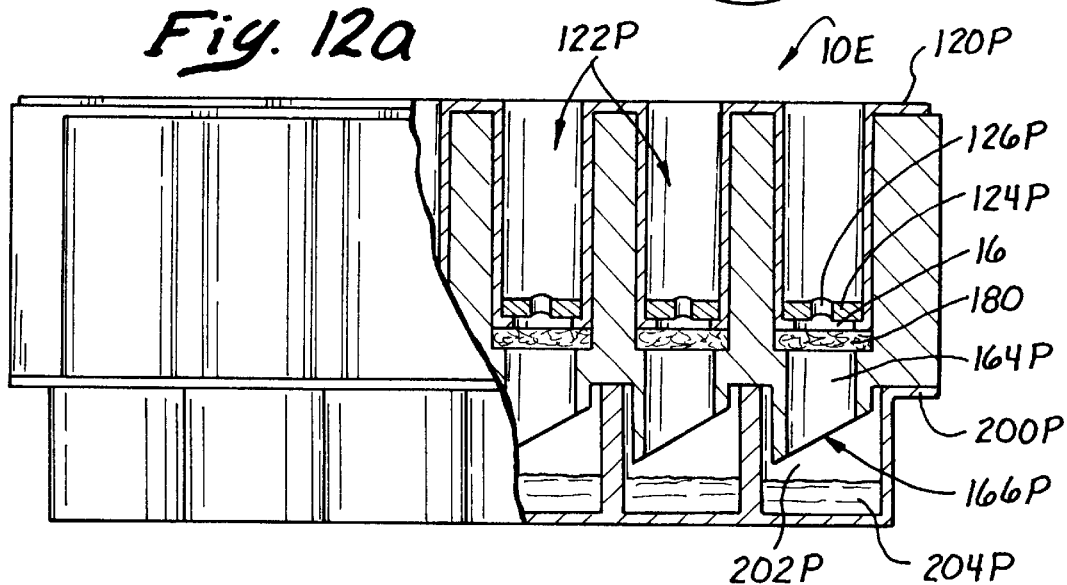

FIGS. 12 and 12a show a preferred type of construction which may be utilized for multiple-sample test kits of the type shown or generally in FIGS. 10 and 11.

With reference to FIGS. 12 and 12a, there is shown a multiple-sample test kit 10e, comprising a receiving vessel tray 120p, a first filter tray 160p and a reagent well base 200p.

Each individual sample receiving vessel 122p formed in the receiving vessel tray 120p has a floor 124p wherein an outlet aperture 126p is formed. It will be appreciated that caps or sealing covering (e.g., one or more sheets of plastic film) may be initially disposed over the under the floor 124p of each sample-receiving vessel 122p such that the desired matrix sample and/or preparation additives may be initially placed in the sample-receiving vessel 122p and mixed without inadvertent leakage out of the outlet apertures 126p, and such caps or closure member(s) may be removed prior to insertion of the individual receiving vessels 122p of the receiving vessel tray 120p into the individual filtration channels 162p of the first filter tray 160p.

As shown in FIG. 12a, when the receiving-vessel tray 120p is so inserted into the filtration tray 160p, the individual sample receiving vessels 122p will extend downwardly within the individual filtration channels 162p such that the floor 124p of each receiving vessel 122p is situated slightly above each filter 180p formed transversely within each filtration channel 162p.

In this preferred mode of construction, generally cylindrical filtration channel extensions 164p extend downwardly below each filter 180p and terminate in angular lower edges 166p. Thus, when the individual filtration channels 162p of the filtration tray 160p are inserted into the individual reagent-containing wells 202p of the reagent well base 200p, the angular lower edges 166p of the lower reagent channel extension 164p will terminate slightly above the liquid level of reagent 204p contained within each reagent-containing well 202p.

It will be appreciated, that the individual reagent containing wells 202p formed in the reagent well base 200p may be independently insertable into and removable from a separate exterior portion of the reagent well base 202a. Such that, in embodiments which employ two or more filtration trays 160p for analysis of two or more analytes, multiple sets of reagent wells 202p may be independently placed within a single exterior housing, and may be used to receive the various filtrates and eluants desired for analysis of multiple analytes in accordance with the above-described methodology of the present invention.

It will be appreciated that the present invention has been described herein with reference with reference to certain presently preferred embodiments and examples only. No effort has been made to describe all possible embodiments in which the invention may be practiced. Accordingly, it is to be understood that various additions deletions modifications and alterations may be made to the above-described embodiments and examples without departing from the intended spirit and scope of the invention. It is, indeed, intended, that all such modifications alterations and deletions be included within the scope of the following claims.

What is claimed:

1. A test kit for determining the presence of at least first and second analytes in a matrix which contains matter other than said first and second analytes, said test kit comprising:
   a first membrane which is operative to prevent some of the matter of said matrix from passing therethrough, while allowing a filtrate containing said analyte to pass therethrough;
   a first receiving vessel positioned in relation to said first membrane so as to receive said filtrate therein; and,
   at least one reagent which is combineable with said filtrate in said receiving vessel to provide a reagent-filtrate admixture from which said analyte may be determined;
   a second membrane interposed between said first membrane and said first receiving well, said second membrane being operative to capture and hold said second analyte while allowing a sub-filtrate containing said first analyte to pass therethrough and into said first receiving well, said second membrane being subsequently positionable adjacent a second receiving well such that a flush solution may be passed through said second membrane such that an eluant containing said second analyte will be received within said second receiving vessel; and,
   at least one reagent which is combineable with the eluant in said second receiving vessel to provide a reagent-eluant admixture from which said second analyte may be determined;
   wherein said first analyte is lipid peroxide and said second analyte is lipid aldehyde, and wherein:
      said first membrane is a microporous membrane which will prevent a portion of said matrix from matrix from passing therethrough, while allowing lipid peroxides and lipid aldehydes to pass therethrough in said filtrate;
      said second membrane is a membrane which will capture and hold lipid aldehydes, while allowing lipid peroxides to pass therethrough in said sub-filtrate;
      said first reagent is xylenol orange such that a xylenol orange-filtrate admixture is provided from wherein the presence of lipid peroxides may be determined by spectrophotometric means; and,
      said second reagent is methyl indole, such that a methyl indole-eluant admixture is provided in which the presence of lipid aldehydes may be determined by spectrophotometric means.

2. The test kit of claim 1 wherein said first membrane is a cellulose ester film having pores of approximately 0.45 microns in size.

3. The test kit of claim 1 wherein said second membrane is a polyamide film having pores of approximately 0.2 microns in size.

4. A test kit for determining the presence of at least first and second analytes in a matrix which contains matter other than said first and second analytes, said test kit comprising:
   a first membrane which is operative to prevent some of the matter of said matrix from passing therethrough, while allowing a filtrate containing said analyte to pass therethrough;
   a first receiving vessel positioned in relation to said first membrane so as to receive said filtrate therein; and,
   at least one reagent which is combineable with said filtrate in said receiving vessel to provide a reagent-filtrate admixture from which said analyte may be determined;
   a second membrane interposed between said first membrane and said first receiving well, said second membrane being operative to capture and hold said second analyte while allowing a sub-filtrate containing said first analyte to pass therethrough and into said first receiving well, said second membrane being subsequently positionable adjacent a second receiving well such that a flush solution may be passed through said second membrane such that an eluant containing said second analyte will be received within said second receiving vessel; and,
   at least one reagent which is combineable with the eluant in said second receiving vessel to provide a reagent-eluant admixture from which said second analyte may be determined;
   wherein said first analyte is lipid peroxide and said second analyte is hexanal, and wherein:
      said first membrane is a microporous membrane which will prevent a portion of said matrix from passing therethrough, while allowing lipid peroxides and hexanal to pass therethrough in said filtrate;
      said second membrane is a membrane which will capture and hold lipid peroxides, while allowing hexanal to pass therethrough in said sub-filtrate;
      said first reagent is a mixture of methyl indole and methane sulfonic acid such that a methyl indole/ methane sulfonic acid-filtrate admixture is provided in which the concentration of hexanal may be determined by spectrophotometric means; and, said second reagent is xylenol orange such that a xylenol orange-eluant admixture is provided in which the presence of lipid peroxides may be determined by spectrophotometric means.

5. The test kit of claim 4 wherein said first membrane is microporous PVDF having pores of approximately 0.45 microns in size.

6. The test kit of claim 4 wherein said second membrane is silica fused glass having pores of approximately 0.2–0.45 microns in size.

7. A test kit for determining the presence of at least first and second analytes in a matrix which contains matter other than said first and second analytes, said test kit comprising:

a first membrane which is operative to prevent some of the matter of said matrix from passing therethrough, while allowing a filtrate containing said analyte to pass therethrough;

a first receiving vessel positioned in relation to said first membrane so as to receive said filtrate therein; and, at least one reagent which is combineable with said filtrate in said receiving vessel to provide a reagent-filtrate admixture from which said analyte may be determined.

a second membrane interposed between said first membrane and said first receiving well, said second membrane being operative to capture and hold said second analyte while allowing a sub-filtrate containing said first analyte to pass therethrough and into said first receiving well, said second membrane being subsequently positionable adjacent a second receiving well such that a flush solution may be passed through said second membrane such that an eluant containing said second analyte will be received within said second receiving vessel; and, at least one reagent which is combineable with the eluant in said second receiving vessel to provide a reagent-eluant admixture from which said second analyte may be determined.

wherein said first analyte is lipid peroxide and said second analyte is conjugated linoleic acid, and wherein:

said first membrane is a microporous membrane which will prevent a portion of said matrix from passing therethrough, while allowing lipid peroxides and conjugated linoleic acid to pass therethrough in said filtrate;

said second membrane is a membrane which will capture and hold conjugated linoleic acid while allowing lipid peroxides to pass therethrough in said sub-filtrate;

said first reagent is xylenol orange such that a xylenol orange-sub-filtrate admixture is provided in which the presence of lipid peroxides may be determined by spectrophotometric means; and, said second reagent is fat red dye, such that a fat red dye-eluant admixture is provided in which the presence of conjugated linoleic acid may be determined by enzyme immunoassay.

8. The test kit of claim 7 wherein said first membrane is microporous nylon having pores of approximately 0.45 microns in size.

9. The test kit of claim 7 wherein said second membrane is nitrocellulose film coated with an antibody to conjugated linoleic acid.

10. A test kit for determining the presence of at least first and second analytes in a matrix which contains matter other than said first and second analytes, said test kit comprising:

a first membrane which is operative to prevent some of the matter of said matrix from passing therethrough, while allowing a filtrate containing said analyte to pass therethrough;

a first receiving vessel positioned in relation to said first membrane so as to receive said filtrate therein; and, at least one reagent which is combineable with said filtrate in said receiving vessel to provide a reagent-filtrate admixture from which said analyte may be determined;

a second membrane interposed between said first membrane and said first receiving well, said second membrane being operative to capture and hold said second analyte while allowing a sub-filtrate containing said first analyte to pass therethrough and into said first receiving well, said second membrane being subsequently positionable adjacent a second receiving well such that a flush solution may be passed through said second membrane such that an eluant containing said second analyte will be received within said second receiving vessel; and, at least one reagent which is combineable with the eluant in said second receiving vessel to provide a reagent-eluant admixture from which said second analyte may be determined;

wherein said first analyte is all chloroacetanilide herbicides and said second analyte is alachlor herbicide and wherein:

said first membrane is a microporous membrane which will prevent a portion of said matrix from passing therethrough while allowing all chloroacetamide herbicides including alachlor to pass therethrough in said filtrate;

said second membrane is a membrane which will capture and hold alachlor while allowing chloroacetanilide herbicides other than alachlor to pass therethrough in said sub-filtrate;

said first reagent is ethylchloroformate such that an ethylchloroformite-sub-filtrate admixture is provided in which the concentration of chloroacetamide herbicides other than alachlor may be determined by spectrophotometric means; and, said second reagent is ethylchloroformite such that an ethylchloroformite-eluant admixture is provided in which the concentration of alachlor may be determined by spectrophotometric means.

11. A method for determining the presence of first and second analyses within a matrix, said method comprising the steps of:

a) passing the matrix through a first membrane to remove extraneous matter therefrom, such that a filtrate containing said first and second analytes will pass through the first membrane;

b) passing the filtrate through a second membrane to capture within said second membrane said first analyte, such that a sub-filtrate containing said second analyte will pass through said second membrane;

c) collecting the sub-filtrate which has passed through said first and second membranes, and combining said sub-filtrate with at least one reagent to provide a sub-filtrate-reagent admixture from which the presence of said first analyte may be determined;

d) eluting the second analyte from the second membrane, and combining such eluant with at least one reagent to provide an eluant-reagent admixture from which the presence of said second analyte may be determined;

e) determining the presence of said first analyte in said sub-filtrate-reagent admixture; and, f) determining the presence of said second analyte in said eluant-reagent admixture;

wherein said first analyte is lipid peroxide and said second analyte is lipid aldehyde, and further wherein:

said first membrane is a microporous membrane which will prevent a portion of said matrix from passing therethrough, while allowing lipid peroxides and lipid aldehydes to pass therethrough in said filtrate;

said second membrane is a membrane which will capture and hold lipid aldehydes, while allowing lipid peroxides to pass therethrough in said sub-filtrate;

said first reagent is xylenol orange such that a xylenol orange-filtrate admixture is provided from wherein the presence of lipid peroxides may be determined by spectrophotometric means; and, said second reagent is methyl indole, such that a methyl indole-eluant admixture is provided in which the presence of lipid aldehydes may be determined by spectrophotometric means.

12. A method for determining the presence of first and second analyses within a matrix, said method comprising the steps of:

a) passing the matrix through a first membrane to remove extraneous matter therefrom, such that a filtrate containing said first and second analytes will pass through the first membrane;

b) passing the filtrate through a second membrane to capture within said second membrane said first analyte, such that a sub-filtrate containing said second analyte will pass through said second membrane;

c) collecting the sub-filtrate which has passed through said first and second membranes, and combining said sub-filtrate with at least one reagent to provide a sub-filtrate-reagent admixture from which the presence of said first analyte may be determined;

d) eluting the second analyte from the second membrane, and combining such eluant with at least one reagent to provide an eluant-reagent admixture from which the presence of said second analyte may be determined;

e) determining the presence of said first analyte in said sub-filtrate-reagent admixture; and, f) determining the presence of said second analyte in said eluant-reagent admixture;

wherein wherein said first analyte is lipid peroxide and said second analyte is hexanal, and further wherein:

said first membrane is a microporous membrane which will prevent a portion of said matrix from passing therethrough, while allowing lipid peroxides and hexanal to pass therethrough in said filtrate;

said second membrane is a membrane which will capture and hold lipid peroxides, while allowing hexanal to pass therethrough in said sub-filtrate;

said first reagent is methyl indole in combination with methane sulfonic acid such that a methyl indole/methane sulfonic acid-filtrate admixture is provided in which the concentration of hexanal maybe determined by spectrophotometric means; and, said second reagent is xylenol orange such that a xylenol orange-eluant admixture is provided in which the presence of lipid peroxides may be determined by spectrophotometric means.

13. A method for determining the presence of first and second analyses within a matrix, said method comprising the steps of:

a) passing the matrix through a first membrane to remove extraneous matter therefrom, such that a filtrate containing said first and second analytes will pass through the first membrane;

b) passing the filtrate through a second membrane to capture within said second membrane said first analyte, such that a sub-filtrate containing said second analyte will pass through said second membrane;

c) collecting the sub-filtrate which has passed through said first and second membranes, and combining said sub-filtrate with at least one reagent to provide a sub-filtrate-reagent admixture from which the presence of said first analyte may be determined;

d) eluting the second analyte from the second membrane, and combining such eluant with at least one reagent to provide an eluant-reagent admixture from which the presence of said second analyte may be determined;

e) determining the presence of said first analyte in said sub-filtrate-reagent admixture; and, f) determining the presence of said second analyte in said eluant-reagent admixture;

wherein said first analyte is lipid peroxide and said second analyte is conjugated linoleic acid, and further wherein:

said first membrane is a microporous membrane which will prevent a portion of said matrix from passing therethrough while allowing lipid peroxides and conjugated linoleic acid to pass therethrough in said filtrate;

said second membrane is a membrane which will capture and hold conjugated linoleic acid while allowing lipid peroxides to pass therethrough in said sub-filtrate;

said first reagent is xylenol orange such that a xylenol orange-sub-filtrate admixture is provided in which the presence of lipid peroxides may be determined by spectrophotometric means; and, said second reagent is fat red dye, such that a fat red dye-eluant admixture is provided in which the presence of conjugated linoleic acid may be determined by enzyme immunoassay.

14. A method for determining the presence of first and second analyses within a matrix, said method comprising the steps of:

a) passing the matrix through a first membrane to remove extraneous matter therefrom, such that a filtrate containing said first and second analytes will pass through the first membrane;

b) passing the filtrate through a second membrane to capture within said second membrane said first analyte, such that a sub-filtrate containing said second analyte will pass through said second membrane;

c) collecting the sub-filtrate which has passed through said first and second membranes, and combining said sub-filtrate with at least one reagent to provide a sub-filtrate-reagent admixture from which the presence of said first analyte may be determined;

d) eluting the second analyte from the second membrane, and combining such eluant with at least one reagent to provide an eluant-reagent admixture from which the presence of said second analyte may be determined;

e) determining the presence of said first analyte in said sub-filtrate-reagent admixture; and, f) determining the presence of said second analyte in said eluant-reagent admixture;

wherein said first analyte is all chloroacetanilide herbicides and said second analyte is alachlor herbicide, and further wherein:

said first membrane is a microporous membrane which will prevent a portion of said matrix from passing therethrough while allowing all chloroacetamide herbicides including alachlor to pass therethrough in said filtrate;

said second membrane is a membrane which will capture and hold alachlor while allowing chloroacetanilide herbicides other than alachlor to pass therethrough in said sub-filtrate;

said first reagent is ethylchloroformate such that an ethylchloroformite-sub-filtrate admixture is provided in which the concentration of chloroacetamide herbacides other than alachlor may be determined by spectrophotometric means; and, said second reagent is ethylchloroformite such that an ethylchloroformite-eluant admixture is provided in which the concentration of alachlor may be determined by spectrophotometric means.

* * * * *